United States Patent [19]
Boeshore et al.

[11] Patent Number: 5,998,702
[45] Date of Patent: Dec. 7, 1999

[54] TRANSGENIC PLANTS EXPRESSING ACC SYNTHASE GENE

[75] Inventors: Maury L. Boeshore, Wauconda, Ill.; Rosaline Z. Deng, Oceanside; Kim J. Carney, Davis, both of Calif.; Glen E. Ruttencutter, DeForest, Wis.; John F. Reynolds, Davis, Calif.

[73] Assignee: Seminis Vegetable Seeds, Inc., Saticoy, Calif.

[21] Appl. No.: 08/860,577

[22] PCT Filed: Jun. 7, 1995

[86] PCT No.: PCT/US95/07271

§ 371 Date: Sep. 22, 1997

§ 102(e) Date: Sep. 22, 1997

[87] PCT Pub. No.: WO96/21027

PCT Pub. Date: Jul. 11, 1996

[51] Int. Cl.[6] .............................. A01H 5/00; A01H 5/10; C07H 21/04; C12N 1/21
[52] U.S. Cl. .................. 800/306; 435/252.2; 435/252.3; 435/320.1; 435/419; 536/23.2
[58] Field of Search .............................. 435/252.3, 320.1, 435/419, 252.2; 536/23.6, 23.2; 800/206, 283, 298, 306, 286

[56] References Cited

U.S. PATENT DOCUMENTS

| | | | |
|---|---|---|---|
| 5,365,015 | 11/1994 | Grierson et al. | 800/205 |
| 5,512,466 | 4/1996 | Klee et al. | 435/172.3 |
| 5,702,933 | 12/1997 | Klee et al. | 435/172.3 |

FOREIGN PATENT DOCUMENTS

| | | |
|---|---|---|
| WO 91/01375 | 2/1991 | WIPO . |
| WO 92/04456 | 3/1992 | WIPO . |
| WO 92/12249 | 7/1992 | WIPO . |

OTHER PUBLICATIONS

Napoli et al. Introduction of a chimeric chalcone synthase gene into petunia results in reversible co–suppression of homologous genes in trans. The Plant Cell. 2:279–289, Apr. 1990.

Wen et al. Nucleotide sequence of a cDNA clone encoding 1–aminocyclopropane–1–carboxylate synthase in mustard (Brassica juncea [L.] Czern & Coss). Plant Physiology. 103:1019–1020, 1993.

Smith et al. Antisense RNA inhibition of polygalacturonase gene expression in transgenic tomatoes. Nature. 34:724–726, Aug. 1988.

David et al. Genetic transformation of cauliflower (Brassica oleracea L. var. Botrytis) by Agrobacterium rhizogenes. Plant Cell Reports. 7:88–91, 1988.

Wagoner, Wendy J., et al., *HortScience* Abstract 348, 27:(6), 620–621 (1992).

EMBL ACC., No. X82273, Rel. 41.(31–10–1994).

*EMBL No.* X72676, (May 1994).

Clarke, Sean F., et al., The influence of 6–benzylaminopurine on post–harvest senescence of floral tissues of broccoli (*Brassica oleracea* var Italica), *Plant Growth Regulation*, 14:21–27, (1994).

Anderson, E.J. et al., Transgenic Plants That Express the Coat Protein Genes of Tobacco Mosaic Virus of Alfalfa Mosaic Virus Interfere with Disease Development of Some Nonrelated Viruses, *The American Phytopathological Society*, 79(11);1284–1289, (1989).

Hampilton, A.J. et al., Identification of a tomato gene for the ethylene–forming enzyme by expression in yeast, *Proc. Natl. Acad. Sci. USA*, 88:7434–7437, (1991).

Kim, Woo Taek, et al., Structure and expression of cDNA As encoding 1–aminocyclopropane–1–carboxylate oxidase homologs isolated from excised mung bean hypocotyls, *Planta*, 194:223–229, (1994).

Larsen, Paul B., et al., Cloning and Nucleotide Sequence of a S–Adenosylmethionin Synthetase cDNA from Carnation[1], *Plant Physiol*, 96:997–999, (1991).

Lawton, Kay A., et al., Molecular Cloning and Characterization of Senescence–Related Genes from Carnation Flower Petals[1], *Plant Physiol.* 90:690–696, (1989).

Gomez–Lim, Miguel Angel, et al.,*Isolation and characterization of a gene involved in ethylene biosynthesis from Arbidopsis thaliana, Gene*, 134:217–221, (1993).

Klee, Harry J., Ripening Physiology of Fruit from Transgenic Tomato (*Lycopersicon esculentum*) Plants with Reduced Ethylene Synthesis, *Plant Physiol*, 102:991–916, (1993).

Picton, Steve, et al., Altered fruit ripening and leaf senescence in tomatoes expressing an antisense ethylene–forming enzyme transgene, *The Plant Journal*, 3(3):469–481, (1993).

Pua, Eng–Chong, et al., Ethylene Regulating Shoot Regenerability in Vitro, *Rice Biotechnology Quarterly*, 21:22–23, (1994).

Woodson, William R., et al., Expression of Ethylene Biosynthetic Pathway Transcript in Senescing Carnation Flowers[1], *Plant Physiol*, 99:0526–0532, (1992).

Nakagawa, Naoki, et al., Cloning of a Complementary DNA for Auxin–Induced 1–Aminocyclopropane–1carboxylate Synthase and Differential Expression of the Gene by Auxin and Wounding, *Plant Cell Physiol*, 32(8):1153–1163, (1991).

Oeller, Paul W., et al., Reversible Inhibition of Tomato Fruit Senescence of Antisense RNA, *Science* 254:437–439, (1991).

(List continued on next page.)

Primary Examiner—Lynette R. F. Smith
Assistant Examiner—Amy J. Nelson
Attorney, Agent, or Firm—Rockey, Milnamow & Katz, Litd.

[57] ABSTRACT

The genomic DNA encoding the ACC synthase of broccoli is provided along with recombinant materials containing constructs of this DNA sequence to permit control of the level of ACC synthase in and, thus, the maturation and aging of *Brassica oleracea* plants which allows one to influence, e.g. lengthen, the shelf-life of these plants.

13 Claims, 11 Drawing Sheets

OTHER PUBLICATIONS

Olson, David, C., et al., Differential Expression of two genes for 1-aminocyclpropane-1-carboxylate synthase in tomato fruits, *Proc. Natl. Acad. Sci. USA*, 88:5340–5344, (1991).

Park, Ky Young, et al., Molecular cloning of an 1-aminocyclopropane-1-carboxylate synthase from senescing carnation flower petals, *Plant Molecular Biology*, 18:377–386, (1992).

Rottmann, William H., et al., 1-Aminocyclopropane-1-Carboxylate Synthase in Tomato is Encoded by a Multigene Family Whose Transcription is Induced During Fruit and Floral Senescence, *J. Mol. Biol.* 222:937–961, (1991).

Lay–Yee M. et al., Isolation of A Putative Full Length cDNA Coding For Apple ACC Synthase, *Plant Physiol*, 102(1): Supp., 1993, Abstract 581.

Masayasu, N., et al., *Biological Abstract* 94(12), Abstract 130960, (1992).

Wagoner, Wendy, J., et al., Superior Regeneration and Agrobacterium Infectability of Broccoli and Cauliflower Tissues and the Identification of A Procedure for the Generation of Transgenic Plants, *HortScience*, 27(6):132–133, (1992).

Luis Herrera–Estrella, Ann Depicker, Marc Van Montagu & Jeff Schell, Expression of chimaeric genes transformed into plant cells using a Ti–plasmid–derived vector, *Nature* vol. 303, May 19, 1983.

Robert T. Fraley, Stephen G. Rogers, Robert B. Horsch, Patricia R. Sanders, Jeffery S. Flick, Steven P. Adams, Michael L. Bittner, Leslie A. Brand, Cynthia L. Fink, Joyce S. Fry, Gerald R. Galluppi, Sarah B. Goldberg, Nancy L. Hoffmann, and Sherry C. Woo, Expression of bacterial genes in plant cells, *Proc. Natl. Acad. Sci. USA* 80 (1983).

Michael Fromm, Loverine P Taylor, and Virgina Walbot, Expression of genes transferred into monocot and dicot plant cells by electroporation, *Proc.Natl.Acad.Sci. USA* vol. 82, pp. 5824–5828, Sep. 1985, Genetics.

Dominique Van Der Straeten, Renato A. Rodrigues–Pousada, Raimundo Villarroel, Susan Hanley, Howard M. Goodman, and Marc Van Montagu, Cloning, genetic mapping, and expression analysis of an *Arabidopsis thaliana* gene encodes 1-aminocyclopropane 1-carboxylate synthase, *Proc.Natl.Acad.Sci. USA* vol. 89, pp. 9969–9973, Oct. 1992 Plant Biology.

Paul W. Oeller, Lu Min–Wong, Loverine P. Taylor, Deborah A. Pike, Athanasios Theologis, Reversible Inhibition of Tomato Fruit Senescence by Antisense RNA, *Science* vol. 254, Oct. 18, 1991.

Jozef St. Schell, Transgenic Plants as Tools to Study the Molecular Organization of Plant Genes, *Science*, vol. 237.

Michael Bevan, Binary Agrobacterium Vectors for plant transformation, *Nucleic Acids Research*, vol. 12, No. 22, 1984.

C.J.S. Smith, C.F. Watson, J. Ray, C.R. Bird, P.C. Morris, W. Schuch & D. Grierson, Antisense RNA inhibition of polygalacturonase gene expression in transgenic tomatoes, *Nature* vol. 334, Aug. 25, 1988.

T.M. Klein, E.D. Wolf, R. Wu & J.C. Sanford, High–velocity microprojectiles for delivering nucleic acids into living cells, *Nature* vol. 327, May 7, 1987.

Joan T. Odell, Frenc Nagy & Nam–Hai Chua, Identification of DNA sequences required for activity of the cauliflower mosaic virus 35S promoter, *Nature* vol. 313, Feb. 28, 1985.

G.M.S. Hooykaas–Van Slogteren, P.J.J. Hooykaas & R.A. Schilperoort, Expression of Ti plasmid genes in monocotyledonous plants infected with *Agrobacterium tumefaciens, Nature* vol. 311, Oct. 25, 1984.

A. Hoekema, P.R. Hirsch, P.J.J. Hooykaas & R.A. Schilperoort, A binary plant vector strategy based on separation of vir–and T–region of the Agrobacterium tumefacient Ti–plasmid, *Nature* vol. 303, May 12, 1983.

F.A. Krens, L. Molendijk, G.J. Wullems & R.A. Schilperoort, In vitro transformation of plant protoplasts with Ti–plasmid DNA, *Nature*, vol. 296, Mar. 4, 1982.

Alexander R. van der Krol, Peter E. Lenting, Jetty Veenstra, Ingrid M. van der Meer, Ronald E. Koes, Anton G.M. Gerats, Joseph N.M. Mol & Antoine R. Stuitje, An anti–sense chalcone synthase gene in transgenic plants inhibits flower pigmentation, *Nature*, vol. 333, Jun. 30, 1988.

Cellular and Developmental Biology Group, Department of Biology, Harvard University, Cambridge, Massachusetts 02138, A general method for site–directed mutagenesis in prokaryotes, *Nature*, vol. 289, 1/8 Jan. 1981.

Takahide Sato, Paul W. Oeller, and Athanasios Theologis, The 1–Aminocyclopropane–1–carboxylate Synthase of Cucurbita, *The Journal of Biological Chemistry*, vol. 266, No. 6, Issue of Feb. 25, pp. 3752–3759, 1991.

Jerry L. Slightom, Mylene Durand–Tardif, Lise Jouanin, and David Tepfer, Nucleotide Sequence Analysis of TL–DNA of Agrobacterium rhizogenes Agropine Type Plasmid, *The Journal of Biological Chemistry*, Fol. 261, No. 1, Issue of Jan. 5, pp. 108–121, 1986.

Robert T. Fraley, Stephen L. Dellaporta, and Demetrios Papahadjopoulos, Liposome–dediated delivery of tobacco mosaic virus RNA into tobacco protoplasts: A sensitive assay for monitoring liposome–protoplast interactions, *Proc.Natl.Acad.Sci. USA* vol. 79, pp. 1859–1863, Mar. 1982 Botany.

D.O. Adams and S.F. Yang, Ethylene biosynthesis: Identification of 1–aminocyclopropane–1–carboxylic acid as an intermediate in the conversion of methionin to ethylene, *Proc.Natl.Acad.Sci. USA* vol. 76, No. 1, pp. 170–174, Jan. 1979 Biochemistry.

Jill Deikman and Robert L. Fischer, Interaction of a DNA binding factor with the 5'–flanking region of an ehtylene–responsive fruit ripening gene from tomato, *IRL Press Limited*, Oxford, England.

Marc De Block, Luis Herrera–Estrella, Marc Van Montague, Jeff Schell and Patricia Zambryski, Expression of foreign genes in regenerated plants and in their progeny, *IRL Press Limited*, Oxford, England.

P. Zambryski, H. Joos, C. Genetello, J. Leemans, M. Van Montagu, and J. Schell, Ti plasmid vector for the introduction of DNA into plant cells without alteration of their normal regeneration capacity. Communicated by M. Van Montagu, Jul. 22, 1983.

Angus G. Hepburn, Janet White, Leslie Pearson, Martin J. Maunders, Lorraine E. Clarke, Andrea G. Prescott and Keith S. Blundy, The use of pNJ5000 as an Intermediate Vector for the Genetic Manipulation of Agrobacterium Ti–plasmids, Journal of General Microbiology (1985), 131, 2961–2969.

Tom Alber and Glenn Kawasaki, Nucleotide Sequence of the Triose Phosphate Isomerase Gene of Saccharomyces cerevisiae, *Journal of Molecular and Applied Genetics* 1:419–434.

Jerry L. Slighton, Custom polymerase–chain–reaction engineering of a plant expression vector, 1991 *Elsevict Science Publishers* B.V. 0378–1119.

Marion M. Bradford, A Rapid and Sensitive Method for the Quantitation of Microgram Quantities of Protein Utilizing the Principle of Protein–Dye Binding, *Analytical Biochemistry* 72, 248–254 (1976).

Ma. Concepcion C. Lizada and Shang Fa Yang, A Simple and Sensitive Assay for 1–Aminocyclopropane–1–Carboxylic Acid, *Analytical Biochemistry* 100, 140–145 (1979).

Anne Crossway, Janette V. Oakes, Jonathan M. Irvine, Barney Ward, Vic C. Knauf and C.K. Shewmaker, Integration of foreign DNA following microinjection of tobacco mesophyll protoplasts, *Mol Gen Genet* (1986) 202:179–185.

Chantal David and Jacques Tempe, Genetic transformation of cauliflower (Brassica oleracea L. var. Botrytis) by Agrobacterium rhizogenes, *Plant Cell Reports* (1988) 7:8j8–91.

Eng–Chong Pua, Cellular and molecular aspects of ethylene on plant morphogenesis of recalcitrant Brassica species in vitro, *Bot.Bull.Acad.Sin.* (1993) 34:191–209.

Michael A. Lawton, Mary A. Tierney, Ikuo Nakamura, Edwin Anderson, Yoshi Komeda, Philip Dube, Nancy Hoffman, Robert T. Fraley and Roger N. Beachy, Expression of a soybean β–conclycinin gene under the control of the Cauliflower Mosaic Virus 35S and 19S promoters in transformed petunia tissues, *Plant Molecular Biology* 9:315–324 (1987).

Toshio Murashige and Folke Skoog, A Revised Medium for Rapid Growth and Bio Assays with Tobacco Tissue Cultures, *Physiologia Plantarum*, vol. 15, 1962.

Keith C. Hall, Mark A. Else & Michael B. Jackson, Determination of 1–aminocyclopropane–1–carboxylic acid (ACC) in leaf tissue and xylem sap using capillary column gas chromatography and a nitrogen/phosphorus detector, *Plant Growth Regulation* 13:225–23, 1993.

M.S. Tian, C.G. Downs, R.E. Lill, and G.A. King., A Role for Ethylene in the yellowing of Broccoli after Harvest, J. *Amer.Soc.Hort.Sci.* 119(2):276–281, 1994.

167 Oral Session 49 (Abstr.347–353) Biotechnology: Genetic Transformation, vol. 27(6), Jun. 1992.

Richard Jorgensen, Keystone Symposium Improved Crop and Plant Products Through Biotechnology, Astract XI–022 (1994).

Athanasios Theologis, Paul W. Oeller, Lu–Min Wong, William H. Rottmann, and David M. Gantz, Use of a Tomato Mutant Constructed with Reverse Genetics to Study Fruit Ripening, a Complex Developmental Process, *Developmental Genetics* 14:282–295 (1993).

Chao–Ming Wen, Mian Wu, Chong–Jin Goh, and Eng–Chong Pua, Nucleotide Sequence of a cDNA Clone Encoding 1–Aminocyclopropane–1–Carboxylate Synthase in Mustard (Brassica juncea [L.] Czern & Coss), *Plant Physiol.* (1993) 103:1019–1020.

Shang Fa Yang and Neil E. Hoffman, Ethylene Biosynthesis and its regulation in higher plants, *Ann.Rev. Plant Physiol.* 1984, 35:155–89.

Joachim Messing, Daniel Geraghty, Gisela Heidecker, Nein– Tai Hu, Jean Kridl, and Irwin Rubenstin, Plant Gene Structure, Department of Biochemistry and Department of Genetics and Cell Biology University of Minnesota St. Paul, Minnesota 55108.

M.J. Holdsworth, W. Schuch and D. Grierson, Nucleotide sequence of an ethylene–related gene from tomato, *Nucleic Acids Research*, vol. 15 No. 24, 1987, 10601.

130960, Nagata, Masayasu, Masamichi Yano and Ryoyasu, Saijo, *Biol Abstr* 94(12):AB–406.

FIG. 1A

```
     Nco I
     CCATGGGATCATCCAAATGGGTCTTGCAGAG<----RMM393
  1  CCATGGGATCAGCCAAATGGGTCTTGCAGAGAATCAGTTTATTATATATTATATACTTTTATCAACCTTTCTTTCAAAAAGTTAATTACATATCGGATATG  100
     H  G  I  S  Q  M  G  L  A  E  N  Q

101  TATTAATCGTTTTTCTCTCGATCATTTTCTATAGGTCTCGTTCGATCTTCTAGAAAGTTACTTAGAGAAGAAAAATCCAGAAGTTTCCATGTGGGATCA   200
                                          V  S  F  D  L  L  E  S  Y  L  E  K  K  N  P  E  V  S  M  W  G  S

201  AAAGGAGCACCTGGGTTCAGAGAAACGCACTGTTTCAAGACTACCACGGTCTCAAATCTTCAGACAAGCTATGGCTTCATGCAACAGATTCGTG         300
     K  G  A  P  G  F  R  E  N  A  L  F  Q  D  Y  H  G  L  K  S  F  R  Q  A  M  A  S  F  M  Q  Q  I  R  G

301  GAGGCAAAGCTAGATTCGACCCTGACCCGTATCGTCCTCACTGCTGGAGCCACAGCCCGCTAATGAACTCTTAACGTTCATCCTCGCTTGATCCCAACGACGC    400
     G  K  A  R  F  D  P  D  R  I  V  L  T  A  G  A  T  A  A  N  E  L  L  T  F  I  L  A  D  P  N  D  A

401  TCTTCTCGTCCCTACGCCCATATTATCCAGGGTACGTCACATTTTATATTATTTAAAATAAAGAATAATTAGTCACTCGTATAGAGATTTTCTATAATATTC   500
     L  L  V  P  T  P  Y  Y  P  G

501  AAAAAATAGCTGCAACTGACACAAACTTAAAATAAAATATTATCTACTATATCTTGTATTTACCGGAAGCGTTTATTTATTTGAATACAGATTCGAT      600
                                                                                                    F  D

601  AGAGATTTGAGATGGAGAACAGGAGTGAGAATTGTACCGATTCATTGCGACAGCTCCAACCATTTTCAGATAACCCCAGAGGGCCTCGAGCAGGCTTACC   700
     R  D  L  R  W  R  T  G  V  R  I  V  P  I  H  C  D  S  S  N  H  F  Q  I  T  P  E  A  L  E  Q  A  Y  Q

701  AAACGGCTCGTGACGCGAACATTAGAGTCCGAGAGTGCTCATAACCAACCCATCGAACCATTAGGCGCAACGGTCCAAAAGAAGGTTCTAGAAGATCT      800
     T  A  R  D  A  N  I  R  V  R  G  V  L  I  T  N  P  S  N  P  L  G  A  T  V  Q  K  K  V  L  E  D  L

801  ACTTGACTTCTGTGTACGCAAGAACATTCACTTGGTCTCCAGACGAGATCTACTCCGGGTCGTCTTCCACGCGTCAGAATTCACCAGCTGTAGCCGAGATC   900
     L  D  F  C  V  R  K  N  I  H  L  V  S  D  E  I  Y  S  G  S  V  F  H  A  S  E  F  T  S  V  A  E  I
```

FIG. 1B

```
 901 GTAGAGAACATCGATGACGTGTCAGTCAAGGAACGTGTCCACATCGTTTACAGCCTCTCCAAAGATCTAGTGCTTCCCGGTTTTCGAGTTGGGACCATTT  1000
       V  E  N  I  D  D  V  S  V  K  E  R  V  H  I  V  Y  S  L  S  K  D  L  V  L  P  G  F  R  V  G  T  I  Y

1001 ACTCGTACAACGATAATGTTGTGAGGACAGCGAGAAGGATGTCGAGTTTCACGCTTGTCTCGTCTCAGACACAACACATGTTGGCTTCCATGTTGTCGGA  1100
       S  Y  N  D  N  V  V  R  T  A  R  R  M  S  S  F  T  L  V  S  S  Q  T  Q  H  M  L  A  S  M  L  S  D

1101 TGAAGAGTTTACGGAGAAGTACATAAGGATAAACCGTGAAAGGCTTAGGAGACGGTACGAGAGACAATTGTGGAAGGGCTTAAGAAGGCAGGATCGAGTGT  1200
       E  E  F  T  E  K  Y  I  R  I  N  R  E  R  L  R  R  R  Y  E  T  I  V  E  G  L  K  K  A  G  I  E  C

1201 TTGAAGGGTAATGCAGGGTTGTTCTGTTGGATGAATTTGGGTTTCTTGACACGAAAACGAAACAAGGCGAGCTTGAGCTTTGGGATGTGATCTTGA      1300
       L  K  G  N  A  G  L  F  C  W  M  N  L  G  F  L  L  D  T  K  T  K  Q  G  E  L  E  L  W  D  V  I  L  K
                                                                                               Nco I
                                               RMM394 → CCTACCAAATCCTAAACGAAACGGTGGTACC
1301 AGGAACTAAAGCTGAATATATCTCCTGGATCTTCGTGCTCCATTGCTCGGAGTATGGAGTATGGATGGTTTAGGATTTGCTTTGCCACCATGG         1384
       E  L  K  L  N  I  S  P  G  S  S  C  H  C  S  E  Y  G  W  F  R  I  C  F  A  T  M
```

FIG. 4

```
     NcoI
GTTTCCATGGGGGGATCAAAAGGAGC<----RMM494
  1 CCATGGGGGGATCAAAAGGAGCCACTGGGTTCAGAGAAACGCCACTGTTCAAGACTACCACGGTCTCAAATCTTTCAGACAAGCTATGCTAGCTTCAT    100
      M  G  G  S  K  G  A  P  G  F  R  E  N  A  L  F  Q  D  Y  H  G  L  K  S  F  R  Q  A  M  A  S  F  M

101 GCAACAGATTCGTGGAGGCAAAGCTAGATTCGACCCGTATCGTCCCACTGCTGGAGCCACAGCCGCTAATGAACTCTTAACGTTCATCCTCGCT          200
      Q  Q  I  R  G  G  K  A  R  F  D  D  P  D  R  I  V  L  T  A  G  A  T  A  A  N  E  L  L  T  F  I  L  A

201 GATCCCAACGACGCTCTTCTCGTCCCCATATTATCCGGATTCGATAGAGATTCAGGATTCGATAGATGGAGAACCGGAGTTGAGAATTGTACCGATTCATTGCG    300
      D  P  N  D  A  L  L  V  P  T  P  Y  Y  P  G  F  D  R  D  L  R  W  R  T  G  V  R  I  V  P  I  H  C  D

301 ACAGCTCCAACCATTTCAGATAACCCCAGAGGCGCTCGAGCAGGCTTACCAAACGGCTCGTGACGGCGAACATTAGAGTCCGAGGAGTGCTCATAACCAA     400
      S  S  N  H  F  Q  I  T  P  E  A  L  E  Q  A  Y  Q  T  A  R  D  A  N  I  R  V  R  G  V  L  I  T  N

401 CCCATCGAACCCATTAGGCGCAACGTCCAAAGAAGTTCTAGAAGATCTACTTGACTTCTGTGTACGCAAGAACATCCACTTGGTCTCAGACGAGATC        500
      P  S  N  P  L  G  A  T  V  Q  K  K  V  L  E  D  L  L  D  F  C  V  R  K  N  I  H  L  V  S  D  E  I

501 TACTCCGGTCGGTCTTCCACGCTCAGAATTCACCAGCGTAGCCGAGATCGTGTCAGTCAAGGAACGTCGATGACGTCAAGAACGTCCACATCGTTT        600
      Y  S  G  S  V  F  H  A  S  E  F  T  S  V  A  E  I  V  E  N  I  D  D  V  S  V  K  E  R  V  H  I  V  Y

601 ACAGCCTCTCCAAAGATCTAGTTCTTCCCGGTTTTCGAGTTGGACCATTACTCGTACAACGATAATGTTGTGAGGACAGCGAGAAGGATGTCGAGTTT      700
      S  L  S  K  D  L  G  L  P  G  F  R  V  G  T  I  Y  S  Y  N  D  N  V  R  T  A  R  R  M  S  S  F

701 CACGCTTGTCTCGTCTCAGACACACAGACCATGTTGCTTCAATGTTGTCGGATGAAGAGTTTACGGAGAAGTACATAAGGATAAACCGTGAAAGGCTTAGG   800
      T  L  V  S  S  Q  T  Q  H  M  L  A  S  M  L  S  D  E  E  F  T  E  K  Y  I  R  I  N  R  E  R  L  R

801 AGAGACGGTACGAGACAATTGTGAAGGCTTAAGAAGGCAGGATCGAGTGTTTGAAGGTAATGCAGGTTTGTTCTGTTGATGAATTGGGTTTCTTGC      900
      R  R  Y  E  T  I  V  E  G  L  K  K  A  G  I  E  C  L  K  G  N  A  G  L  F  C  W  M  N  L  G  F  L  L
                                                                                                         NcoI
                                                     RMM491--->GGACTAGAAGCACGTACCGAGCC
901 TCGACACGAAAACGAAACAAGGCGAGCTCGAGCTTTGGGATGTGATCTTGGAGGAACTAAAGCTGAATATATCTCCTGATCTTCGTCGTGCCATGGC      994
      D  T  K  T  Q  G  E  L  E  L  W  D  V  I  L  E  E  L  K  L  N  I  S
```

FIG. 5A

```
              1
Bjunceacdna   CGGGCAACAG AACAACAAAA AAACACAGCT TATTAAAACC CCTTTGAGGA AACAAGAGAA ACAAAAATGG TAGCTTTGAC TGCAGAGAAG CAAGATCAGA   100
Acccdnatop    .......... .......... .......... .......... .......... .......... .......... .......... .......... ..........

101
Bjunceacdna   ACCTACTGTC AAGAATGGCC GCCGGTGACG GTCACGGCGA GAATTCAGCT TATTTCGACG GCTGAAAGC  TTATGAAGAA AACCCATTTC ACCCAATTAA   200
Acccdnatop    .......... .......... .......... .......... .......... .......... .......... .......... .......... ..........

201
Bjunceacdna   CAGACCCGAT GGAGTTATTC AGATGGGTCT CGCTGAAAAT CAGCTTTGTG GAGATTTGAT GCGTAAATGG GTTTTAGAAC ATCCAGAAGC TTCGATTTGC   300
Acccdnatop    .......... .......... .......... .......... .......... .......... .......... .......... ........GT TTCCATGGGG 301
Bjunceacdna   ACAGCAGAAG GTGTGAATCA GTTCAGCGAC ATTGCAATTT TCCAGGACTA CCATGGCTTG CCCGAGTTCA GACAAGCTGT AGCGAAGTTT ATGGAGAAGA   400
Acccdnatop    GGATCAAAAG GAGCACCTGG GTTCAGAGAA AACCACTGT  TTCAAGACTA CCACGGCTC  AAATCTTTCA GACAAGCTAT GGCTAGCTTC ATGCAACAGA 401
Bjunceacdna   CAAGAAACAA CAAAGTGAGG TTTGATCCTG ATCGGATTGT CATGAGCGGC GGTGCAACCG GAGCACACGA GACGGTTGCT TTCTGTTTAG CCAATACCGG   500
Acccdnatop    TTCGTGGAGG CAAAGCTAGA TTCGACCCTG ACCGTATCGT CCTCACTGCT GGAGCACACAG CCGCTAATGA ACTCTTAAGG TTCATCCTCG CTGATCCCAA 501
Bjunceacdna   CGAAGGTTTC TTGGTTCCGA CTCCTTATTA TCCAGGGTTT GATAGAGATT TGAGATGGAG AACCGGAGTG AATCTTGTAC CGGTTACTTG TCATAGCTCT   600
Acccdnatop    CGACGCTCTT CTCGTCCCTA CGCCATATTA TCCAGGATTC GATAGAGATT TGAGATGGAG AACCGGAGTG AGAATTGTAC CGATTCATTG CGACAGCTCC 601
Bjunceacdna   AACGGGTTTA AGATCACGGT GGAAGCCTTG GAAGCTGCGT ACGAAAACGC GGTGTATCC  AACATTCCCG TTAAGGGTTT ACTCATAACC AATCCTTCGA   700
Acccdnatop    AACCATTTTC AGATAACCCC AGAGGCGCTC GAGCAGGCTT ACCAAACGGC TCGTGACGCG AACATTAGAG TCCGAGGAGT GCTCATAACC AACCCATCGA
```

FIG. 5B

```
         701                                                                                            800
Bjunceacdna  ACCCGCTTGG TACGACGTTA GACCGGGATT GCTTGAAATC TTTGGTTAAC TTCACCAATA ACAAGGGAT CCACCTCATT GCTGATGAGA TCTATGCAGC
Acccdnatop   ACCATTAGG CGCAACGGTC CAAAGAAGG TTCTAGAAGA TCTACTTGAC TTCTGTGTAC GCAAGAACAT CCACTTGGTC TCAGACGAGA TCTACTCCGG
         801                                                                                            900
Bjunceacdna  CACTACTTTT GGTCAATCCG AGTTCATAAG TGTTGCAGAA GTCATCGAGG ...TTCGAAC CGGATTTGA TCCATATTGT GTATAGCCTA
Acccdnatop   GTCGGTCTTC CACGCGTCAG AATTCACCAG CGTAGCCGAG ATCGTAGAGA ACATCGATGA CGTGTCAGTC AAGGAACGTG TCCACATCGT TTACAGCCTC
         901                                                                                            1000
Bjunceacdna  TCAAAAGATA TGGGTTTGCC CGGTTTAAGA GTCGGTATAG TATACTCTTA CAATGACCGG GTGGTTCAAA TTGCTAGGAA AATGTCGAGT TTCGGTTTGG
Acccdnatop   TCCAAAGATC TAGGTCTTCC CGGTTTTTCC GTTGGGACCA TTTACTCGTA CAACGATAAT GTTGTGAGGA CAGCGAGAAG GATGTCGAGT TTCACGCTTG
        1001                                                                                            1100
Bjunceacdna  TCTCGTCTCA AACCCAGCAT CTGATCGCCA AAATGTTATC CGACGAAGAC TTTGTAGACG AATTCATCCG CAAGAGCAAA CTACGGTTAG CTGCAAGACA
Acccdnatop   TCTCGTCTCA GACCAACAC ATGTTGGCTT CCATGTTGTC GGATGAAGAG TTTACGGAGA AGTACATAAG GATAAACCGT GAAAGGCTTA GGAGACGGTA
        1101                                                                                            1200
Bjunceacdna  CGCAGAGTTA ACAACCGGTT TAGACGGTTT AGGCATTGGT TGGTTAAAGG CCGGAGCCGG TTTGTTCATC TGGATGGATT TAAGAAACCT TTTGAAGACA
Acccdnatop   CGAGACAATT GTGGAAGGGC TTAAGAAGGC AGGGATCGAG TGTTTGAAGG GTAATGCAGG TTGTTCTGT TGGATGAATT TGGGTTTCTT GCTCGACACG
        1201                                                                                            1300
Bjunceacdna  GCTACATTCG ACTCAGAGAT GGAGCTGTGG CGTGTGATCG CTACCAACAA GGTGAAGCTT AACGTTTCTC CAGGCGGTTC GTGCCATTGC AACGAACCGG
Acccdnatop   AAAACGAAAC AAGGCGAGCT CGAGCTTTGG GATGTGATC. ..TTGGAGGA ACTAAAGCTG AATATATCTC C.TGATCTTC GTGCCATGGC TCGGAGCCGA
        1301                                                                                            1400
Bjunceacdna  GATGGTTTAG TATGTTTGCG AACATGGACC ACAAGACCAT GGAGACAGCT CTAGAGAGGA TCAGAGTGTT CACTAGTCAA CTTGAGGAGG AGAGTCTGAA
Acccdnatop   ATTCT.....
        1401                                                                                            1500
Bjunceacdna  ACAGACTAAA CCAATGGCTG CACCAACTGT GATGGCTAAG AAGAAGATGT GTTGGCAGAG TAGCCTCCGG TTAAGCTTTA AGGACACGAG ACGTTTCGAG
Acccdnatop
```

FIG. 6A

```
   1 CCATGGGATCAGCAGCCAAATGGGTCTTGCAGAGAATCAGTTATTATATTATATACTTTTATCAACCTTTCTTTCAAAAAAGTTAATTACATATCGGATATG    100

101 TATTAATCGTTTTTCTCTCGATCATTTTCTATAGTCTCGTTCGATCTTCTAGAAAGTTACTTAGAGAAGAAAAATCCAGAAGTTTCCATGTGGGGATCA    200
                                                                                 5' GTTTCCATGGGGGATCA <--RMM494
                                                                                    ||||| |||||||
                                                                                    CCATGGGGGATCA
                                                                                     M  G  G  S

AAAGGAGC 3' <--RMM494
 201 AAAGGAGCACCTGGGTTCAGAGAAAACGCACTGTTTCAAGACTACCACGGTCTCAAATCTTTCAGACAAGCTATGGCTAGCTTCATGCAACAGATTCGTG    300
     ||||||||||||||||||||||||||||||||||||||||||||||||||||||||||||||||||||||||||||||||||||||||||||||||||
     AAAGGAGCACCTGGGTTCAGAGAAAACGCACTGTTTCAAGACTACCACGGTCTCAAATCTTTCAGACAAGCTATGGCTAGCTTCATGCAACAGATTCGTG
      K  G  A  P  G  F  R  E  N  A  L  F  Q  D  Y  H  G  L  K  S  F  R  Q  A  M  A  S  F  M  Q  Q  I  R  G

301 GAGGCAAAGCTAGATTCGACCCTGACCCGTATCGTCCTCCACTGCTCTGGAGCCACAGCCGCTAATGAACTCTTAACGTTCATCCTCGCTGATCCCAACGACGC    400
     ||||||||||||||||||||||||||||||||||||||||||||||||||||||||||||||||||||||||||||||||||||||||||||||||||||||
     GAGGCAAAGCTAGATTCGACCCTGACCCGTATCGTCCTCCACTGCTCTGGAGCCACAGCCGCTAATGAACTCTTAACGTTCATCCTCGCTGATCCCAACGACGC
      G  K  A  R  F  D  P  D  R  I  V  L  T  A  G  A  T  A  A  N  E  L  L  T  F  I  L  A  D  P  N  D  A

401 TCTTTCTGTCCCTACGCCATATTATCCAGGGTACGTCACATTTTATATTATTTAAATAAAGAATAATTAGTCACTCGTATAGAGATTTCTATAATATTC    500
     |||||||||||||||||||||||||||||||
     TCTTTCTGTCCCTACGCCATATTATCCAGG
      L  L  V  P  T  P  Y  Y  P  G

501 AAAAAATAGCTGCAACTGACACAAACTTAAAATAAATATTATCTACTATATCTTGTATTTACCGGAACGTTTATTTATTGAATACAGATTCGAT    600
                                                                                     ||||||
                                                                                     ATTCGAT
                                                                                      F  D
```

FIG. 6B

```
601 AGAGATTTGAGATGGAGAACAGGAGTGAGAATTGTACCGATTCATTGCCGACAGCTCCAACCATTTCAGATAACCCAGAGGCCGCTCGAGCAGGCTTACC
    ||||||||||||||||||||||||||||||||||||||||||||||||||||||||||||||||||||||||||||||||||||||||||||||||||  700
    AGAGATTTGAGATGGAGAACAGGAGTGAGAATTGTACCGATTCATTGCGACAGCTCCAACCATTTCAGATAACCCAGAGGCGCTCGAGCAGGCTTACC
    R D L R W R T G V R I V P I H C D S S N H F Q I T P E A L E Q A Y Q

701 AAACGGCTCGTGACGCGAACATTAGAGTCCGAGGAGTGCTCATAACCAACCCATTGAACCTGAACCGTCCAAAAGAAGCGTTCTAGAAGATCT
    |||||||||||||||||||||||||||||||||||||||||||||||||||||||||||||||||||||||||||||||||||||||||||  800
    AAACGGCTCGTGACGCGAACATTAGAGTCCGAGGAGTGCTCATAACCAACCCATTGAACCTGAACCGTCCAAAAGAAGCGTTCTAGAAGATCT
    T A R D A N I R V R G V L I T N P S N P L G A T V Q K K V L E D L

801 ACTTGACTTCTGTGTACGCAAGAACATTCACTTGGTCTCCAGACGAGATCTACTCCGGGTCGGTCTTCCACGCGTCAGAATTCACCAGCGTAGCCGAGATC
    |||||||||||||||||||||||||||||||||||||||||||  ||||||||||||||||||||||||||||||||||||||||||||||||||||||  900
    ACTTGACTTCTGTGTACGCAAGAACATTCACTTGGTCTCCAGAGATCTACTCCGGGTCGGTCTTCCACGCGTCAGAATTCACCAGCGTAGCCGAGATC
    L D F C V R K N I H L V S D E I Y S G S V F H A S E F T S V A E I

901 GTAGAGAACATCGATGACGTGTCAGTCAAGGAACGTGTCCACATCGTTTACAGCCTCTCCAAAGATCTAGTCTTCCCGGTTTTCGAGTTGGGACCATTT
    |||||||||||||||||||||||||||||||||||||||||||||||||||||||||||||||||||||||||||||||||||||||||||||||||  1000
    GTAGAGAACATCGATGACGTGTCAGTCAAGGAACGTGTCCACATCGTTTACAGCCTCTCCAAAGATCTAGTCTTCCCGGTTTTCGAGTTGGGACCATTT
    V E N I D D V S V K E R V H I V Y S L S K D L G L P G F R V G T I Y
```

FIG. 6C

```
1001 ACTCGTACAACGATAATGTTGTGAGGACAGCGAGAAGGATGTCGAGTTTCACGCTTGTCTCGTCTCAGACACAACACATGTTGGCTTCCATGTTGTCGGA
     ||||||||||||||||||||||||||||||||||||||||||||||||||||||||||||||||||||||||||||||||||||||||||||||||||
     ACTCGTACAACGATAATGTTGTGAGGACAGCGAGAAGGATGTCGAGTTTCACGCTTGTCTCGTCTCAGACACAACACATGTTGGCTTCCATGTTGTCGGA       1100
     S  Y  N  D  N  V  V  R  T  A  R  R  M  S  S  F  T  L  V  S  S  Q  T  Q  H  M  L  A  S  M  L  S  D

1101 TGAAGAGTTTACGGAGAAGTACATAAGGATAAACCGTGAAAGGCTTAAGAGACGGTACGAGACAATTGTGAAGGCAGGGATCGAGTGT
     |||||||||||||||||||||||||||||||||||||||||||||||||||||||||||||||||||||||||||||||||||||||
     TGAAGAGTTTACGGAGAAGTACATAAGGATAAACCGTGAAAGGCTTAAGAGACGGTACGAGACAATTGTGAAGGCAGGGATCGAGTGT           1200
     E  E  F  T  E  K  Y  I  R  I  N  R  E  R  L  R  R  R  Y  E  T  I  V  E  G  L  K  K  A  G  I  E  C

1201 TTGAAGGGTAATGCAGGGTTGTTCTGTTGGATGAATTTGGGTTTCTTGCTCGACACGAAAACGAAACAAGGCGAGCTCGAGCTTTGGGATGTGATCTTGA
     |||||||||||||||||||||||||||||||||||||||||||||||||||||||||||||||||||||||||||||||||||||||||||||||||||
     TTGAAGGGTAATGCAGGGTTGTTCTGTTGGATGAATTTGGGTTTCTTGCTCGACACGAAAACGAAACAAGGCGAGCTCGAGCTTTGGGATGTGATCTTGG  1300
     L  K  G  N  A  G  L  F  C  W  M  N  L  G  F  L  L  D  T  K  T  K  Q  G  E  L  E  L  W  D  V  I  L  E

1301 AGGAACTAAAGCTGAATATATCTCCCTGGATCTTCGTGCCATTGCTCGGAGTATGGATGGTTTAGGATTTGCTTTGCCACCATGG   1384
     |||||||||||||||||||||||||||||||||||||||||
     AGGAACTAAAGCTGAATATATCTCCT GATCTTCGTGCCATGG
     E  L  K  L  N  I  S
                         3' GGA CTAGAAGCACGGTACCGAGCC 5' <--RMM491
```

TRANSGENIC PLANTS EXPRESSING ACC SYNTHASE GENE

FIELD OF THE INVENTION

This invention relates to the plant enzyme ACC synthase which is essential for the production of ethylene in higher plants. More particularly, the invention relates to the DNA sequence of a *Brassica oleracea* ACC synthase, DNA constructs containing this sequence, plant cells containing the constructs and plants derived therefrom.

BACKGROUND OF THE INVENTION

The enzyme ACC synthase is essential to the production of ethylene in higher plants. It is well known that ethylene is related to various events in plant growth and development including fruit ripening, seed germination, abscission, and leaf and flower senescence. Ethylene production is strictly regulated by the plant and is induced by a variety of external factors known as ethylene-inducible events. These include the application of auxins, wounding, anaerobic conditions, viral infection, elicitor treatment, chilling, drought, and exposure to ions such as cadmium and lithium ions. In addition, it recently has been shown that ethylene production begins after harvest (Tian et al., *J. Amer. Soc. Hort. Sci.*, 119:276–281 (1994)).

The pathway for ethylene synthesis in plants was first described by Adams and Yang, *PNAS, U.S.A.*, 76:170–174 (1979) who identified 1-aminocyclopropane-1-carboxylic acid as an intermediate in the conversion of methionine to ethylene. The physiology and biochemistry of ethylene synthesis was extensively reviewed by Yang and Hoffman in *Ann. Rev. Plant Physiol.*, 35:155–189 (1984). In the ethylene biosynthetic pathway, methionine is catalyzed by the enzyme S-adenosylmethionine synthetase to form S-adenosylmethionine (SAM). SAM is then converted to 1-aminocyclopropane-1-carboxylic acid (ACC) by the enzyme ACC synthase. This three-membered-ring amino acid is then metabolized to yield ethylene, a reaction catalyzed by the enzyme ACC oxidase.

The ethylene-forming enzyme genes in tomato were the first to be isolated. Smith et al., *Planta*, 168:94–100 (1986) reported the rapid appearance of an mRNA correlated with ethylene synthesis, which encodes a protein of molecular weight 35,000. This formed the basis for the development of a number of molecular strategies to inhibit ethylene formation in certain transgenic plants. One such method is based on antisense RNA.

As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited by the presence in the cell of "antisense RNA." The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of anti-sense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature*, 333:866–869 (1988)); or at a more subtle biochemical level, e.g., change in the amount of polygalacturonase and reduction in depolymerization of pectin during tomato fruit ripening (Smith et al., *Nature*, 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology," Abstract X1-022 (1994)). Thus, both antisense and sense RNA have been proven to be useful in achieving downregulation of gene expression in plants.

SUMMARY OF THE INVENTION

The invention provides a DNA molecule in purified and isolated form comprising DNA encoding the ACC synthase of *Brassica oleracea* plant, such as broccoli, cabbage, cauliflower, brussel sprouts, kale, kohlrabi, etc. The invention also provides chimeric plant expression cassettes, i.e., constructs, comprising a DNA molecule encoding the ACC synthase of *Brassica oleracea*, a promoter and polyadenylation signal functional in plant cells wherein the DNA molecule encoding the ACC synthase of *Brassica oleracea* is operably linked to said promoter and polyadenylation signal, effective to transcribe sense and antisense RNA from the DNA encoding said ACC synthase when employed to transform the genome of a host cell, and to recombinant host cells transformed with this expression cassette. The host cells transformed with this expression cassette can include *Agrobacterium tumefaciens* and *Agrobacterium rhizogenes* cells. The invention also provides transformed *B. oleracea* and *Cucumis melo* plants and plant parts, such as seeds. The invention further provides a method to control ACC synthase production and, thus, the growth and development of *Brassica oleracea* and *Cucumis melo* plants, comprising transforming the plants with a chimeric expression cassette with a DNA molecule encoding *B. oleracea* ACC synthase operably linked to a promoter and polyadenylation signal functional in plants, effective to transcribe sense or antisense RNA from the DNA encoding said ACC synthase. The invention thus provides a method for controlling the maturation and aging of *Brassica oleracea* and *Cucumis melo* plants which allows one to influence, e.g., lengthen, the shelf-life of these plants and fresh vegetable products derived from these plants.

As used herein, with respect to a DNA molecule or "gene," the phrase "isolated and purified" means that the molecule is either extracted from its context in the plant genome by chemical means and purified and/or modified to the extent that it can be introduced into the present cassettes in the appropriate orientation, i.e., sense or antisense. As used herein, the term "chimeric" refers to two or more DNA molecules which are derived from different sources, strains, or species, which do not recombine under natural conditions, or to two or more DNA molecules from the same species, which are linked in a manner that does not occur in the native genome. Thus, the present constructs and vectors permit the augmentation of plant genomes with a limited number of preselected genes. As used herein, "recombinant" refers to a nucleic acid molecule which has been obtained by manipulation of genetic material using restriction enzymes, ligases, and similar recombinant techniques as described by, for example, Sambrook et al., *Molecular Cloning: A Laboratory Manual*, Second Edition (1989) Cold Spring Harbor Laboratory Press, Cold Spring Harbor. "Recombinant," as used herein, does not refer to naturally occurring genetic recombinations. As used herein, the term "express" or "expression" is defined to mean transcription alone.

BRIEF DESCRIPTION OF THE FIGURES

FIGS. 1A–1B illustrate the nucleotide sequence of, and the amino acid sequence encoded by, a genomic DNA clone, ACCA1, of *Brassica oleracea* ACC synthase [SEQ ID NO:1 and 2, 3 and 4] and the oligomer primers used to amplify ACC synthase sequences from total plant DNA. (RMM393 and RMM394 [SEQ ID NOS:5 and 6, respectively]). The PCR primers contain novel NcoI restriction enzyme cloning sites.

FIG. 4 illustrates the nucleotide and amino acid sequences encoded by *Brassica oleracea* ACC synthase cDNA clone TA13 [SEQ ID NO:7 and 8]. The cDNA clone was obtained using oligomers RMM494 and RMM491 [SEQ ID NO: 9 and 10, respectively].

FIGS. 5A–5B illustrate a nucleotide sequence comparison of *Brassica oleracea* ACC synthase cDNA clone TA13 and a *Brassica juncea* ACC synthase cDNA ("Bjunceacdna" in the Figure, Wen et al., *Plant Physiol.*, 103:1019–1020 (1993) SEQ ID NO:11). The alignment was obtained using the UWGCG Program Pileup. The dots represent gaps in homology between the two sequences or lack of sequence data.

FIGS. 6A–6C illustrate an alignment of the nucleotide sequence of *Brassica oleracea* ACC synthase cDNA clone TA13 [SEQ ID NO:7] and *Brassica oleracea* ACC synthase clone ACCA1 [SEQ ID NO:1]. The amino acid sequence encoded by TA13 is shown [SEQ ID NO:8]. The location of the two primers employed to obtain a cDNA clone are shown (RMM494 and RMM491) [SEQ ID NO: 9 and 10, respectively].

DETAILED DESCRIPTION OF THE INVENTION

Figure 2:
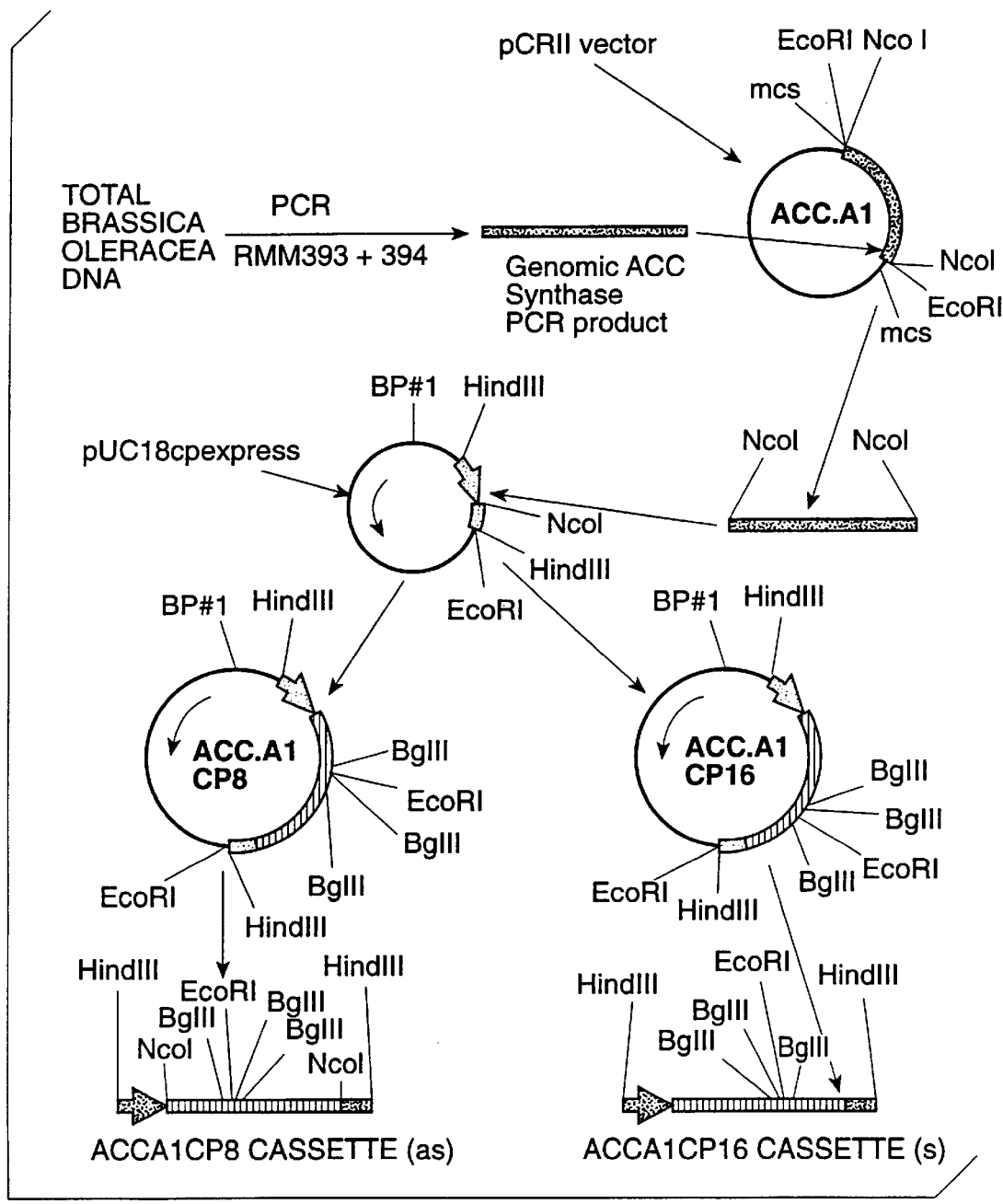
FIG. 2 illustrates a flow chart showing the steps used to insert the *Brassica oleracea* ACC synthase genomic DNA coding sequence, both in the sense and the antisense orientation, into plant expression cassettes.

As stated above, the present invention provides a DNA molecule that encodes the ACC synthase of *Brassica oleracea* plants. To practice the present invention, the ACC synthase gene must be isolated from the genome and inserted into a vector. Thus, the present invention provides an isolated and purified DNA molecule that encodes ACC synthase. As used herein, a DNA molecule that encodes ACC synthase includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes ACC synthase, for example, includes the DNA molecule having the nucleotide sequence of FIG. 1 [SEQ ID NO:1], a DNA molecule complementary to the nucleotide sequence of FIG. 1 [SEQ ID NO:1], as well as a DNA molecule which also encodes ACC synthase and its complement which hybridizes with an ACC synthase-specific DNA probe in hybridization buffer with 6×SSC, 5× Denhardt's reagent, 0.5% SDS and 100 µg/ml denatured, fragmented salmon sperm DNA and remains bound when washed at 68° C. in 0.1×SSC and 0.5% SDS (Sambrook et al., *Molecular Cloning: A Laboratory Manual*, 2nd ed. (1989)). Moreover, the DNA molecules of the present invention can include other noncoding nucleotides that do not interfere with expression of the ACC synthase gene. Preferably, the isolated and purified DNA molecules of the present invention comprise a coding region for ACC synthase. Thus, preferably the DNA molecules of the present invention are those "consisting essentially of" DNA that encodes ACC synthase.

Once a *Brassica oleracea* ACC synthase gene is isolated and amplified, a ACC synthase fragment can be produced in a variety of recombinant systems. The gene is placed into an expression vector which can be transformed into plant cells. This can then be used in a method of inhibiting ethylene inducible events in a plant. Specifically, the method involves: providing a transgenic plant stably transformed with an exogenous chimeric DNA construct comprising DNA of *Brassica oleracea* ACC synthase placed in an orientation relative to a promoter in the chimeric DNA construct so that antisense RNA is transcribed; and culturing said transgenic plant under conditions so that said DNA is transcribed to antisense RNA. Alternatively, the method involves: providing a transgenic plant stably transformed with an exogenous chimeric DNA construct comprising DNA of *Brassica oleracea* ACC synthase placed in an orientation relative to a promoter in the chimeric DNA construct so that sense RNA is transcribed; and culturing said transgenic plant under conditions so that said DNA is transcribed to sense RNA.

The ACC synthase gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant.

Plants harboring an expression vector can be assayed to determine whether the transgenic plants produce elevated levels of sense or antisense RNA and if aspects of plant development which are ethylene sensitive have been affected, and in particular, if plant senescence has been delayed. Plants stably transformed with expression vectors containing either genomic- or cDNA-derived ACC synthase sequences can be assayed for expression of recombinant ACC synthase sequences and/or for ACC synthase levels in said plants by methods well known in the art.

Using methods well known in the art, a quantity of *Brassica oleracea* genomic DNA is isolated. Polymerase chain reactions can be used to amplify the DNA encoding the ACC synthase gene with the use of oligomer primers specific for the ACC synthase gene. These primers can include novel restriction sites used in subsequent cloning steps. PCR amplified fragments are inserted into cloning vectors, such as well-characterized plasmids, which are then used to transform *E. coli* and create a DNA library.

To isolate a cDNA clone of a ACC synthase of *Brassica oleracea*, *Brassica oleracea* polyA+ RNA is isolated, and a cDNA library is created using the RNA, by methods known to the art. The RNA is incubated with primers that hybridize to the RNA and reverse transcriptase, and a complementary DNA molecule is produced. A DNA complement of the complementary DNA molecule is produced and that sequence represents a DNA copy (cDNA) of the original RNA molecule. The DNA complement can be produced in a manner that results in a single double stranded cDNA or polymerase chain reactions can be used to amplify the DNA encoding the cDNA with the use of oligomer primers specific for the ACC synthase gene. These primers can include novel restriction sites used in subsequent cloning steps. Thus, a double stranded DNA molecule is generated which contains the sequence information of the ACC synthase RNA. The double stranded DNA molecules are inserted into cloning vectors, such as well-characterized plasmids, which are then used to transform *E. coli* and create a cDNA library.

Previously identified ACC synthase genes can be used as hybridization probes to screen the library to determine if any of the transformed bacteria contain DNA fragments with sequences coding for the ACC synthase. Alternatively, plasmids can be screened by restriction enzyme digests to determine if the desired sequences are present. The inserts in any bacterial colonies which contain this region can be sequenced.

Because neither genomic or cDNA clones contain transcription and translation signals necessary for expression once transferred and integrated into a plant genome, they must, therefore, be engineered to contain a plant expressible promoter, a translation initiation codon (ATG), and a plant functional poly(A) addition signal (AATAAA) 3' of its translation termination codon. Thus, for expression in plants, the chimeric expression cassette will contain in addition to the ACC synthase-encoding DNA sequence, a plant promoter region, a transcription initiation site (if the coding sequence to be transcribed lacks one), and a transcription termination sequence. Unique restriction enzyme sites at the 5' and 3' ends of the cassette are typically included to allow for easy insertion into a pre-existing construct, such as a plasmid or phage.

Any of a number of transcription initiation regions (i.e., promoters) that direct transcription in plant cells is suitable. The promoter can be either constitutive or inducible. It can be of bacterial origin, viral origin, or eukaryotic origin, such as plant origin.

Promoters of bacterial origin include the octopine synthase promoter, the nopaline synthase promoter and other promoters derived from native Ti plasmids (Herrera-Estrella et al., *Nature*, 303:209–213 (1983)). The nopaline synthase (Nos) promoter has been shown to be active in at least the following monocot and dicot plants with edible parts: apple, *Malus pumila*; cauliflower, *Brassica oleracea*; celery, *Apium graveolens*; cucumber, *Cucumis sativus*; eggplant, *Solanum melongena*; lettuce, *Lactuca sativa*; potato, *Solanum tuberosum*; rye, *Secale cereale*; strawberry, *Fragaria xananassa*; tomato, *Lycopersicon esculentum*; and walnut, *Juglans regia*.

Viral promoters include the 35S and 19S RNA promoters of cauliflower mosaic virus (O'Dell et al., *Nature*, 313:810–812 (1985)). The cauliflower mosaic virus (CaMV) 35S promoter has been shown to be highly active in many plant organs and during many stages of development when integrated into the genome of transgenic plants including tobacco and petunia, and has been shown to confer expression of foreign genes in protoplasts of both dicots and monocots. For example, the CaMV 35S promoter has been demonstrated to be active in at least the following monocot and dicot plants with edible parts: blackberry, Rubus; blackberry/raspberry hybrid, Rubus, and red raspberry; carrot, *Daucus carota*; maize; potato, *Solanum tuberosum*; rice, *Oryza sativa*; strawberry, *Fragaria xananassa*; and tomato, *Lycopersicon esculentum*.

In addition, plant promoters such as ribulose-1,3-diphosphate carboxylase, flower organ-specific promoters, heat shock promoters, seed-specific promoters, promoters that are transcriptionally active in associated vegetable tissue, etc. can also be used. Organ-specific promoters are also well known. For example, the E8 promoter is only transcriptionally activated during tomato fruit ripening, and can be used to target gene expression in ripening tomato fruit (Deikman and Fischer, *EMBO J.*, 7:3315 (1988)). The activity of the E8 promoter is not limited to tomato fruit, but is thought to be compatible with any system wherein ethylene activates biological processes. Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, *Trans. R. Soc. London*, B314:343 (1986)).

DNA sequences controlling eukaryotic gene expression have been extensively studied. Promoter sequence elements include the TATA box consensus sequence (TATAAT), which is usually 20–30 base pairs (bp) upstream of the transcription start site. In most instances, the TATA box is required for accurate transcription initiation. By convention, the start site is called +1. Sequences extending in the 5' (upstream) direction are given negative numbers and sequences extending in the 3' (downstream) direction are given positive numbers. In plants, further upstream from the TATA box, at positions −80 to −100, there is typically a promoter element with a series of adenines surrounding the trinucleotide G (or T)NG (Messing, J. et al., in *Genetic Engineering in Plants*, Kosage, Meredith and Hollaender, eds. (1983) pp. 221– 227). Other sequences conferring tissue specificity, response to environmental signals, or maximum efficiency of transcription may also be found in the promoter region. Such sequences are often found within 400 bp of transcription initiation site, but may extend as far as 2000 bp or more.

In the construction of chimeric promoter/structural gene cassettes, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the gene to provide for efficient termination. The termination region may be obtained from the same gene as the promoter sequence or may be obtained from different genes.

If the mRNA transcribed from the gene is to be efficiently processed, DNA sequences which direct polyadenylation of the RNA are also commonly added to the vector construct (Albert and Kawaski, *Mol. and Appl. Genet.,* 1:419–434 (1982)). Polyadenylation is of importance for expression of the ACC synthase-encoding RNA in plant cells. Polyadenylation sequences include, but are not limited to, the *Agrobacterium octopine* synthase signal (Gielen et al., *EMBO J.,* 3:835–846 (1984)), and the nopaline synthase signal (Depicker et al., *Mol. and Appl. Genet.,* 1:561–573 (1982)). Replication sequences, of bacterial or viral origin, are generally also included to allow the cassette to be cloned in a bacterial or phage host.

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as *E. coli.* Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

A number of techniques are available for transformation of plants or plant cells. All types of plants are appropriate subjects for "direct" transformation. Most dicot species can be transformed in vitro by Agrobacterium as well as species which are a natural plant host for Agrobacterium. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311:763–764). However, there is growing evidence now that certain monocots can be transformed by Agrobacterium.

In one form of direct transformation, the cassette is microinjected directly into plant cells by use of micropippettes to mechanically transfer the recombinant DNA (Crossway, *Mol. Gen. Genetics,* 202:179–185 (1985)). In another form, the genetic material is transferred into the plant cell using polyethylene glycol (Krens, et al., *Nature,* 296:72–74 (1982)). In yet another form of direct transformation, the genetic material is transferred using high velocity ballistic penetration by small particles with the nucleic acid either within the matrix of small beads or particles, or on the surface (Klein, et al., *Nature,* 327:70–73 (1987)). In still another method, protoplasts are fused with other entities which contain the DNA whose introduction is desired. These entities are minicells, cells, lysosomes or other fusible lipid-surfaced bodies (Fraley, et al., *Proc. Natl. Acad. Sci. U.S.A.,* 79:1859–1863 (1982)). DNA may also be introduced into the plant cells by electroporation (Fromm et al., *Proc. Natl. Acad. Sci. U.S.A.,* 82:824 (1985)). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate.

For transformation mediated by bacterial infection, a plant cell is infected with *Agrobacterium tumefaciens* or *Agrobacterium rhizogenes* previously transformed with the DNA to be introduced. Agrobacterium is a representative genus of the gram-negative family Rhizobiaceae. Its species are responsible for crown gall (*A. tumefaciens*) and hair root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science,* 237:1176–1183 (1987)). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature,* 303:179–189 (1983)). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell. Construction of recombinant Ti and Ri plasmids in general follows methods typically used to introduce additional DNA into the more common bacterial vectors, such as pBR322. Additional use can be made of accessory genetic elements sometimes found with the native plasmids and sometimes constructed from foreign sequences. These may include, but are not limited to, "shuttle vectors" (Ruvkum and Ausubel, *Nature,* 298:85–88 (1981)), promoters (Lawton et al., *Plant Mol. Biol.,* 9:315–324 (1987)), and structural genes for antibiotic resistance as a selection factor (Fraley et al., *Proc. Natl. Acad. Sci.,* 80:4803–4807 (1983)).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J.*, 3:1681–1689 (1984) and the non-oncogenic Ti plasmid pGV2850 described by Zambryski et al., *EMBO J.*, 2:2143–2150 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research*, 12:8711–8721 (1984), and the non-oncogenic Ti plasmid PAL4404 described by Hoekema, et al., *Nature*, 303:179–180 (1983). Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Plant cells that have been transformed can also be regenerated using known techniques. Plant regeneration from cultured protoplasts is described in Evans et al., *Handbook of Plant Cell Cultures*, Vol. 1:MacMillan Publishing Co. New York, 1983; and Vasil I. R. (ed.), *Cell Culture and Somatic Cell Genetics of Plants*, Acad. Press, Orlando, Vol. I, 1984, and Vol. II, 1986. It is known that practically all plants can be regenerated from cultured cells or tissues, including but not limited to, all major species of sugar cane, sugar beet, corn, cotton, fruit trees, and legumes. The regenerated plants are transferred to soil and cultivated in a conventional manner.

A large number of plants have been shown capable of regeneration from transformed individual cells to obtain transgenic whole plants. For example, regeneration has been shown for dicots as follows: apple, *Malus pumila;* blackberry, Rubus; Blackberry/raspberry hybrid, Rubus; red raspberry, Rubus; carrot, *Daucus carota;* cauliflower, *Brassica oleracea;* celery, *Apium graveolens;* cucumber, *Cucumis sativus;* eggplant, *Solanum melongena;* lettuce, *Lactuca sativa;* potato, *Solanum tuberosum;* rape, *Brassica napus;* soybean (wild), *Glycine canescens;* strawberry, *Fragaria xananassa;* tomato, *Lycopersicon esculentum;* walnut, *Juglans regia;* melon, *Cucumis melo;* grape, *Vitis vinifera;* mango, *Mangifera indica;* and for the following monocots: rice, *Oryza sativa;* rye, *Secale cereale;* and maize.

In addition, regeneration of whole plants from cells (not necessarily transformed) has been observed in: apricot, *Prunus armeniaca;* asparagus, *Asparagus officinalis;* banana, hybrid Musa; bean, *Phaseolus vulgaris;* cherry, hybrid Prunus; grape, *Vitis vinifera;* mango, *Mangifera indica;* melon, *Cucumis melo;* okra, *Abelmoschus esculentus;* onion, hybrid Allium; orange, *Citrus sinensis;* papaya, *Carrica papaya;* peach, *Prunus persica* and plum, *Prunus domestica;* pear, *Pyrus communis;* pineapple, *Ananas comosus;* watermelon, *Citrullus vulgaris;* and wheat, *Triticuim aestivum.*

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated into regenerated transgenic plants, it can be transferred to other plants by sexual crossing. Any of a number of standard breeding techniques can be used, depending upon the species to be crossed. The plants are grown and harvested using conventional procedures.

Most of the recombinant DNA methods employed in practicing the present invention are standard procedures, well known to those skilled in the art. Restriction endonucleases are obtained from commercial sources and are used according to the vendor's recommendations or other variations known to the art. Reagents, buffers, and culture conditions are also known to those in the art. General references containing such standard techniques include the following: R. Wu, ed. (1979) *Methods in Enzymology*, Vol.68; J. H. Miller (1972) *Experiments in Molecular Genetics;* D. M. Glover, ed. (1985) *DNA Cloning*, Vol. II; S. B. Gelvin and R. A. Schilperoort, eds. *Introduction, Expression, and Analysis of Gene Products in Plants;* and Sambrook et al., *Molecular Cloning: A Laboratory Manual*, Second Edition (1989) Cold Spring Harbor Laboratory Press, Cold Spring Harbor, all of which are incorporated by reference.

The invention will be further described by reference to the following detailed examples. All reagents are commercially available from sources such as Sigma Chemical Co., unless otherwise stated.

EXAMPLE 1

A. Extraction of Total Cellular DNA From Broccoli by a CTAB Extraction Method

Three or four newly expanding leaves of broccoli (0.5–1 gm fresh weight) were placed into the bottom corner of a ZIPLOC brand bag. One mL of preheated CTAB extraction buffer was added to the leaf sample. CTAB extraction buffer (1% (w/v) CTAB Sigma H-5882; 1.4 M NaCl; 100 mM Tris HCl pH 8.0; 30 mM EDTA pH 8.0) was prepared and preheated to 65° C. 5–10 minutes prior to use. The following was added to each mL of CTAB extraction buffer just before using: 10 $\mu$L of 2-mercaptoethanol, 6 $\mu$L of Ribonuclease $T_1$ (5,000 U/ml) Sigma R-8251, and 25 $\mu$L of Ribonuclease A (10 mg/ml) Sigma R-4875.

The ZIPLOC brand bag was placed flat on a hard surface. A one-liter Corning media-bottle was firmly rolled across the surface of the bag repeatedly until the leaf tissue was disrupted and had the consistency of applesauce. The macerated sample was moved to a bottom corner of the ZIPLOC brand bag and the corner was cut with a scissors. The entire sample was squeezed into a sterile 15-mL Falcon tube and incubated at 70° C. for 30 minutes. The sample was cooled for 5 minutes at room temperature. One mL of chloroform-octanol (24:1, v/v) was added, and the sample was vortexed for 1 second to mix thoroughly. The samples were then centrifuged in a Beckman GH 3.7 rotor (Beckman GPR centrifuge) at 2500 rpm, 25° C. for 5 minutes to separate phases. The aqueous phase (approximately 1000 $\mu$l) was then transferred to a sterile 1.5-mL Eppendorf tube and 1.5

μL of RNAse T$_1$ (10 mg/mL) was added. An equal volume of 1% CTAB precipitation buffer was added to each sample. The tube was inverted a few times and incubated at room temperature for 30 minutes.

The sample was centrifuged in an Eppendorf microfuge for 60 seconds to pelletize the precipitate. The supernatant was discarded, and the tube was inverted on a paper towel to drain. Following this, 500 μL of a high salt solution (10 mM Tris pH 8.0, 1 M NaI, 1 mM EDTA pH 8.0) was added, and the sample was incubated at 65° C. for 15 minutes to dissolve the DNA. One mL of 100% ethanol was added and the sample was placed at −20° C. for one hour, or overnight if desired, to precipitate DNA. DNA was hooked or spooled with a 1.5-mL capillary pipet and placed into a sterile 1.5-mL Eppendorf tube. The DNA pellet was washed by adding 1 mL of wash solution (80% ethanol, 15 mM ammonium acetate) and incubated at room temperature for 15 minutes. The washed DNA was dissolved in 300 μL of sterile water.

B. PCR Amplification of Target Genomic ACC Synthase

Polymerase chain reactions (PCRs) were carried out using reagents supplied with the Perkin Elmer Cetus Gene Amp PCR Kit under the following conditions: approximately 0.1 μg/mL total cellular DNA of *Brassica oleracea*, 1.5 mM MgCl, 24 μg/mL of each oligomer primer, 200 μM each DNTP, kit reaction buffer, and AmpliTaq DNA polymerase supplied with the kit. Reaction tubes were subjected to 93C. for 1 minute, 55C. for 1 minute, then 72C. for 3 minutes for 30 cycles in a Perkin Elmer Thermocycler. Oligonucleotides used to prime the PCR were modeled after sequences of a cDNA clone of the ACC synthase gene found in *Arabidopsis thaliana* (Van der Straten et al., *Proc. Nat'l. Acad. Sci U.S.A.*, 89:9969–9973 (1992)). Oligomer primers RMM393 (5'-CCATGGGATCATCCAAATGGGTCTTGCAGAG-3' [SEQ ID NO:3], which is complementary to the 5' end of the cDNA clone of *Arabidopsis thaliana* ACC synthase gene) and RMM394 (5'-CCTACCAAATCCTAAA-CGAAACGGTGGTACC-3' [SEQ ID NO:4], which is complementary to the 3' end of the cDNA clone of *Arabidopsis thaliana* ACC synthase gene), were used to prime this reaction (FIG. 1).

C. Cloning Genomic ACC Synthase PCR Fragment into the pCRII Vector

The genomic ACC synthase PCR DNA fragment was cloned into the pCRII vector supplied with the TA Cloning Kit, purchased from Invitrogen Corporation, San Diego, Calif., to obtain a clone known as ACCA1 (FIG. 2). The sequence of the inserted gene in ACCA1 was determined by nucleotide DNA sequencing using a U.S. Biochemical (Cleveland, Ohio) dideoxy sequencing kit (FIG. 1) [SEQ ID NO:1]. In an effort to determine the intron/exon structure of the genomic ACC synthase DNA sequence, the deduced amino acid sequence of the *Brassica oleracea* genomic clone ACCA1 was compared with the published amino acid sequence of *Arabidopsis thaliana* ACC synthase. Three complete exons and two introns were identified in genomic clone ACCA1.

A *Brassica juncea* ACC synthase cDNA clone published by Wen et al., *Plant Physiol.*, 103:1019–1020 (1993) was compared to the *Brassica oleracea* genomic clone ACCA1 (FIG. 1). The relatedness of conserved portions of these two sequences showed that the ACCA1 clone encoded an ACC synthase. The structure of *Brassica oleracea* ACC synthase is highly related to the intron/exon arrangement in the tomato genomic ACC synthase clone GTOMA (Holdsworth et. al., *Nuc. Acids Res.*, 15:10600 (1987)).

D. Insertion of the ACC Synthase Coding Sequence into an Expression Cassette (cp Express)

To begin transfer of the genomic *Brassica oleracea* ACC synthase gene into a plant expression cassette, ACCA1 was digested with NcoI to produce a 1380 bp NcoI fragment encoding genomic *Brassica oleracea* ACC synthase. Using standard methods (see Slightom, *Gene*, 100:251–255 (1991)), this fragment was inserted into the expression cassette pUC18cp in an antisense orientation to obtain ACCA1CP8 and in the sense orientation to obtain ACCA1CP16 (FIG. 2).

E. Insertion of Genomic ACC Synthase DNA Cassettes into a Binary Vector

Figure 3A:
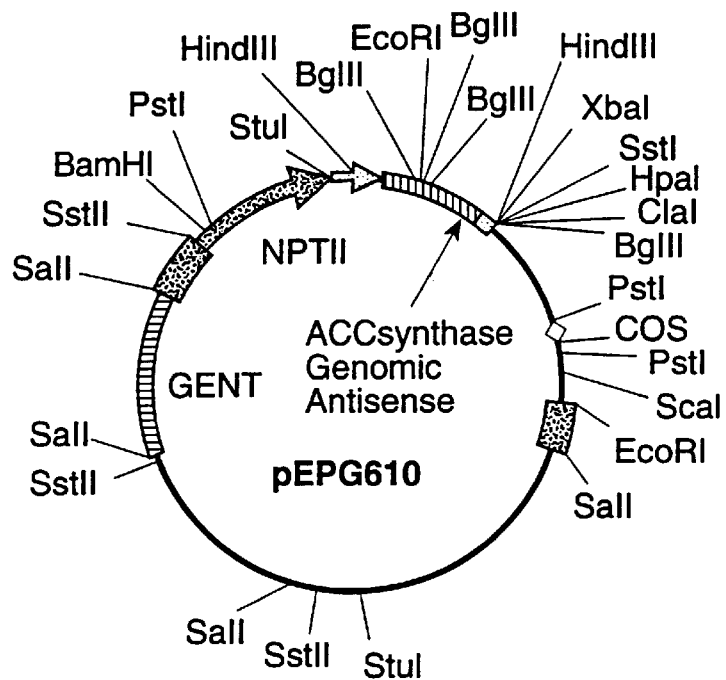
FIGS. 3A–3B illustrate the binary plasmids pEPG611 and pEPG610, which function as cassettes, containing the sense cassette ACCA1CP16 and the antisense cassette ACCA1CP8, respectively.
Figure 3B:
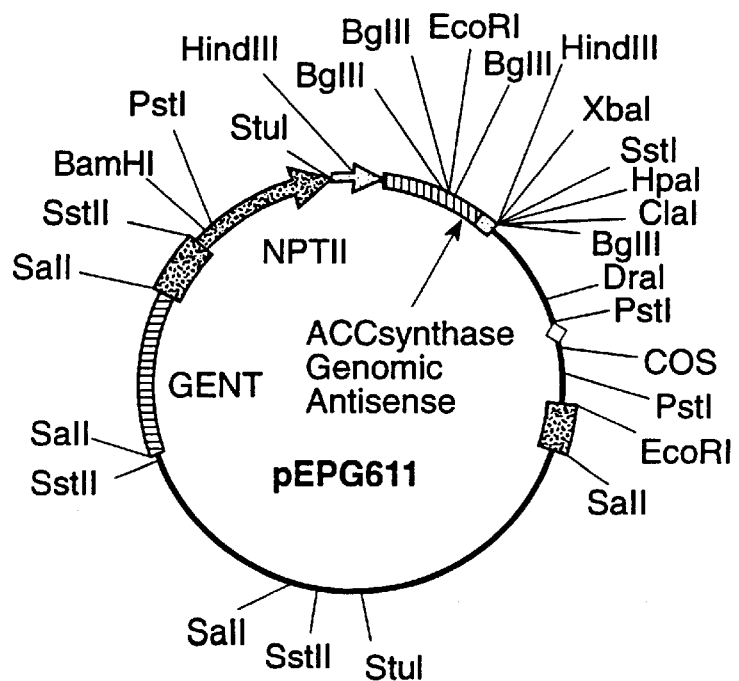
Figure 7:
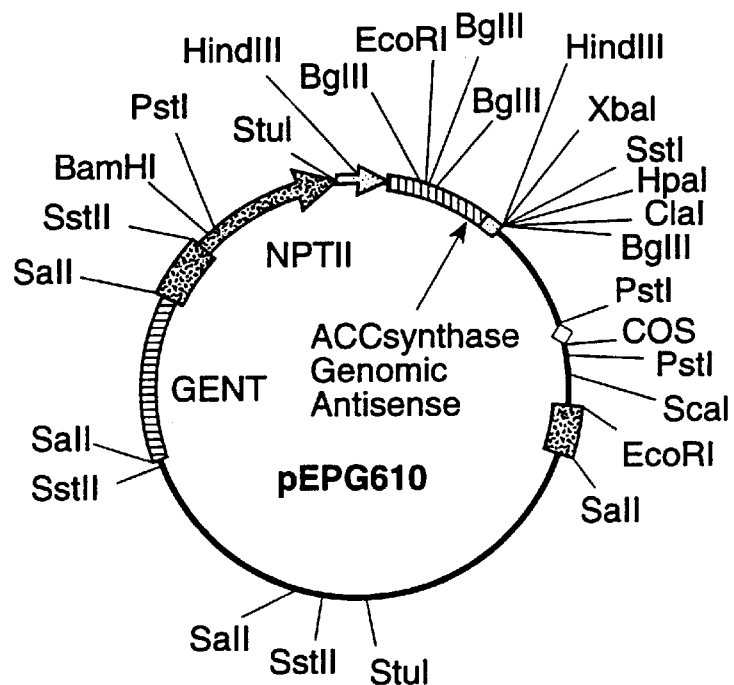
FIG. 7 illustrates the restriction map of PEPG 610.
Figure 8:
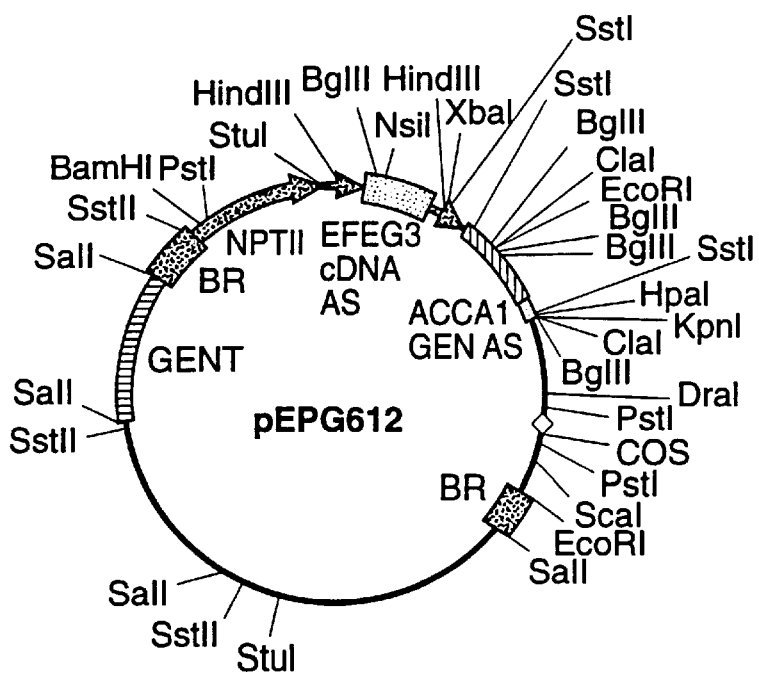
FIG. 8 illustrates the restriction map of PEPG 612.

HindIII fragments harboring the full-length cDNA clone inserted in the antisense and sense cassettes were isolated. The antisense cassette ACCA1CP8 (FIG. 2) was inserted into the unique HindIII site of binary vector pGA482G to produce plasmid pEPG610 (FIG. 3, for further information regarding pGA482G, see Applicants' Assignees copending patent application Ser. No. 08/366,991, entitled "Transgenic Plants Expressing DNA Constructs Containing a Plurality of Genes to Impart Virus Resistance" filed on Dec. 30, 1994, incorporated by reference herein). The sense cassette ACCA1CP16 (FIG. 2) was inserted into the unique HindIII site of binary vector pGA482G to produce plasmid pEPG611 (FIG. 3). The structures shown in FIG. 3 were verified by restriction analysis.

F. Transformation of the Binary Vectors into *Brassica oleracea* Plants by Agrobacteria-Mediated Transformation The binary plasmids pEPG610 and pEPG611 are transformed into strains of *Agrobacterium tumefaciens*, e.g., strain C58Z707 and *Agrobacterium rhizogenes*, e.g., strain A4RC in preparation for *Brassica oleracea* transformation procedures. Strain C58Z707 was obtained from Augus Hepburn at Indiana University, Bloomington, Ind. (Hepburn et al., *J. Gen. Micro.*, 131:2961–2969 (1985)). Strain A$_4$RC was obtained from Jerry Slightom, The Upjohn Company, Kalamazoo, Mich. Evidence of the origin of the strain A$_4$ is presented by Slightom et al.,*J. Biol. Chem.*, 261(1):108–121 (1986). The resulting Acrobacterium strain is used to perform *Brassica oleracea* plant transformation procedures. Agrobacterium-mediated transfer of the plant expressible *Brassica oleracea* ACC synthase is done using procedures known to those skilled in the art (For example see David et al., *Plant Cell Reports*, 7:88–91 (1988) and Damgaard et al., *Plant Molecular Biology*, 17:1–8 (1991)). Specifically, aseptically grown hypocotyls with or without an intact root system are inoculated with engineered *A. tumefaciens* or *A. rhizogenes*. Hypocotyls are then transferred to MS medium (Murashige et al., *Physiol Plantarum*, 15:473–497 (1962)) containing 200 micromolar acetosyringone. Two to three days later, hypocotyls are transferred to MS medium containing 50 mg/L kanamycin sulfate, 500 mg/L carbenicillin and 200 mg/L cefotaxime (MS-O). Hypocotyls are continuously subcultured every 21 days on MS-O medium until shoots form. Shoots are then removed from agar and potted in soil. Transgenic plants (R$_0$) are grown to sexual maturity in a greenhouse and R$_1$ transgenic seed is produced.

G. Evaluation of Transgenic Plants for Inhibition of Ethylene Biosynthesis

The transformation of R$_0$ plants and their segregating progeny is verified by routine methods. These include ELISA assays for NPTII protein detection and DNA assays such as PCR amplification (detection) and Southern blot hybridization for detection of the foreign DNA.

For example, protein in leaf tissue samples taken from R$_1$ transgenic broccoli seedlings is extracted and analyzed for NPTII protein by enzyme-linked immunosorbant assay (ELISA). The procedure and kit supplied by 5 Prime→3 Prime, Inc., Boulder, Colo., is used to assay NPTII expression in $R_1$ transgenic broccoli seedlings. In an initial screen of $R_1$ transgenic seedlings for NPTII protein by ELISA, all independent transgenic proprietary Brassica oleracea lines express NPTII. The data indicate that these initial lines are segregating for the NPTII marker gene.

Evaluation of transgenic plants for inhibition of ethylene biosynthesis can be accomplished by assaying transgenic Brassica oleracea materials for expression of ACC synthase sense or antisense RNA using Northern blotting or a RNase protection assay. In a Northern blot of transgenic materials, RNA extracted from transgenic Brassica oleracea is subjected to agarose electrophoresis and blotted onto a Nylon membrane. Radioactive $^{32}$P-labelled antisense RNA or $^{32}$P-labelled sense RNA probes were synthesized in vitro and used to hybridize the blot. Only antisense RNA of the ACC synthase transgene in the plant will bind to the $^{32}$P-labelled sense RNA probe; thus antisense ACC synthase RNA will be detected by autoradiography. Parallel hybridization of replicate blots with antisense ACC synthase RNA probe serves as a check on the hybridization with the sense RNA probe. Likewise, only sense RNA of the ACC synthase transgene in the plant will bind to the $^{32}$P-labelled antisense RNA probe; thus sense ACC synthase RNA will be detected by autoradiography. Parallel hybridization of replicate blots with sense ACC synthase RNA probe serves as a check on the hybridization with the antisense RNA probe.

The RNase protection assay involves hybridizing a labelled RNA molecule (pure sequence synthesized in vitro) with total tissue RNA in solution in a tube. Only complementary RNA will hybridize with the pure RNA labelled and synthesized in vitro. The total pool of RNA is subjected to RNase A and RNase $T_1$ digestion; protected mRNAs are resistant to RNase digestion. Protected mRNAs are evaluated quantitatively and qualitatively on an acrylamide gel.

Following the determination of whether Brassica oleracea ACC synthase antisense or sense RNA is expressed, the transgenic materials or tissues are assayed for ACC synthase activity. The biochemical detection of ACC synthase can be performed as described by Sato et al., J. Biol. Chem., 266:3752–3759 (1991). The enzyme sample is incubated with 200 μM AdoMet (S-adenosylmethionine), 10 μM pyridoxal phosphate, 40 μg BSA (bovine serum albumin) in 200 mM Hepes buffer pH 8.5, in a total volume of 600 μL in a 12×75 mm test tube at 30° C. for 30 minutes. The amount of ACC formed is assayed according to Lisada et al., Anal. Biochem., 100:140–150 (1979). The protein concentration is determined according to Bradford, Anal. Biochem., 72:248–254 (1976) using bovine gamma-globulin IgG as a standard. Hall et al. (Plant Growth Regulation, 13:225–230 (1993)) report an alternative method of measuring ACC levels in plant materials. Very briefly, the method involves the following steps: 1) homogenization of plant materials in appropriate extraction medium containing 80% (v/v) methanol and butylated hydroxytoluene (as an antioxidant); 2) addition of $^{14}$C ACC to the extracts; 3) preliminary purification using a small, strongly acidic, ion exchange column (Bondelute SCX 3CC); 4) esterification with acidified n-propanol, and benzoylation with benzoic anhydride in pyridine at 110° C.; 5) pyridine evaporation, followed by HPLC purification; and 6) measurement for recovery by radioactive scintillation counting.

In addition, it is possible to employ immunological methods (for example, ELISA or Western blots) to assay transgenic materials for levels of ACC synthase protein. It is expected that transgenic materials would exhibit reduced levels of ACC synthase protein compared with non-transgenic materials. Tian et al., J. Amer. Soc. Hort. Sci., 119:276–281 (1994) outline in some detail their procedures for evaluating "degreening" in response to ethylene in harvested broccoli. They measured chlorophyll content in the florets after harvest.

H. Brassica oleracea ACC Synthase cDNA Gene Constructions cDNA fragments of ACC synthase were obtained by PCR amplification of ACC fragments from total cDNA. Briefly, the process involved the following steps: 1) isolation of total RNA from broccoli heads (florets); 2) enrichment for polyA+ RNA; 3) synthesis of single-stranded cDNA; 4) polymerase chain reaction amplification of target ACC synthase sequences; 5) cloning an ACC synthase PCR fragment into the PCRII vector; 6) insertion of the ACC synthase coding sequence into an expression cassette (cp express) in sense or antisense orientation; 7) insertion of an ACC synthase cassette into a binary vector; 8) transformation of the binary vector into Agrobacterium; 9) transfer of the construct into Brassica oleracea plants by Agrobacteria-mediated transformation; and 10) evaluation of transgenic plants for inhibition of ethylene biosynthesis.

First, total RNA was isolated from broccoli florets (heads) by the use of Tri-Reagent and the instructions provided with the reagent (Molecular Research Center, Inc). Second, polyA+ RNA was enriched by oligo dT cellulose chromatography. Briefly, the procedure involves mixing total broccoli floret RNA (this includes messenger RNA or polyA+ RNA) with oligo dT-cellulose in 20 mM NaCl and Tris buffer. The oligo-dT cellulose is washed to eliminate non-polyadenylated RNAs from the cellulose. Subsequently, RNA enriched for polyA+ RNA is eluted from the cellulose by elution in Tris buffer that includes no NaCl.

Third, single-stranded cDNA was synthesized using polyA+ RNA template. The reaction included 1×First Strand cDNA Synthesis Buffer (GIBCO-BRL), 1 mM dNTP's (USB), 1 μg oligo dT, 1 μL RNasin (Promega), 3.3 uM dithiothreitol, 5 μL $^{32}$PdCTP (3000 Ci-mmol, NENDuPont NEGo13H), and 1 μL RTase Superscript (GIBCO-BRL). Single-stranded B. oleracea cDNA was purified by the use of columns (Quiaquick-spin PCR column) obtained from Qiagen. The first strand cDNA reaction was characterized by hydroxide agarose gel electrophoresis; based on electrophoretic mobility it was estimated that the size distribution of first strand cDNA centered near 1 kilobase.

Fourth, an ACC synthase cDNA fragment (approximately 1 kb in length) was PCR amplified with the use of the cDNA template obtained as above. The polymerase chain reaction (PCR) was carried out using reagents supplied with the Perkin Elmer Cetus Gene Amp PCR Kit under the following conditions: ~50 ng (estimated) total cDNA of Brassica oleracea, 2.0 mM $MgCl_2$, 12 μg/mL of each oligomer primer, 800 μM each dNTP, kit reaction buffer, and Ampli-Taq DNA polymerase supplied with the kit. Reaction mixtures were first subjected to 98° C. for 1 minute, then 93° C. for 45 seconds, 55° C. for 45 seconds, and 72° C. for 1.5 minutes for five cycles, then 93° C. for 45 seconds, 52° C. for 45 seconds, and 72° C. for 1.5 minutes for 33 cycles, and finally 72° C. for five minutes in a Perkin Elmer Thermocycler. Oligomer primers RMM491 and RMM494 were used to prime this reaction (FIG. 4).

The reaction yielded a 1-kb fragment which was subsequently gel-purified and cloned into the cloning vector PCRII (Invitrogen Corporation) by methods well known to those skilled in the art. By restriction analysis two ACC synthase cDNA clone candidates were identified. Nucleotide sequence analysis of clone ACCcDNA TA13 confirmed that the insert encodes ACC synthase (FIG. 5). The ACC synthase cDNA sequences from clone ACCcDNA TA13 are then placed into pUC18cpexpress for antisense RNA or for sense RNA expression in transgenic plants.

Melons were made transgenic for B. oleracea ACC oxidase and ACC synthase antisense constructs to inhibit ethylene production in climacteric fruit and extend shelf-life. *Brassica oleracea* ACC synthase antisense constructs were transferred to melon (*Cucumis melo*) plants via Agrobacteria-mediated transformation using procedures published by Fang and Grumet (1990 and 1993). The following constructs were transformed into melon: pEPG610 and pEPG612.

After shoots were regenerated on kanamycin-containing solid tissue culture media, they were rooted and tested for transformation status. Transformation status was verified either by testing regenerated organized shoots for ability to form callus on kanamycin-containing solid media (only transformed materials expressing NPTII can grow on this media) or by NPTII expression detected by ELISA.

Inbred cantaloupe line 10 was used to produce 29 experimental transgenic plant lines containing the pEPG610 plasmid contract, 27 of which are viable potted plants. Inbred cantaloupe line CA96 was used to produce 32 experimental transgenic plant lines containing the pEPG612 plasmid construct, all of which are viable potted plants. Inbred cantaloupe line 1077 was used to produce 7 experimental transgenic plant lines, containing the pEPG612 plasmid construct, all of which are viable potted plants.

The complete disclosures of all patents, patent documents, and publications are incorporated herein by reference, as if individually incorporated by reference. While specific embodiments of the invention have been described, it should be apparent to those skilled in the art that various modifications thereof can be made without departing from the true spirit and scope of the invention. Accordingly, it is intended that the following claims cover all such modifications within the full inventive concept.

In addition to the transgenic melons obtained with the use of ACC synthase constructs (eg., pEPG610 and 612), transgenic red cabbage plants are also being produced with the use of ACC synthase constructs. Constructs being used for red cabbage transformation are included in the list below. Currently, shoots are being recovered from transformation procedures; these will be rooted shortly and evaluated for ACC synthase RNA production.

| pEPG Plasmid | Genes | # Shoots Regenerated |
|---|---|---|
| pEPG610 | ACC Syn Geno (As) | 1 |
| pEPG611 | ACC Syn Geno (S) | 3 |
| pEPG613 | ACC Syn cDNA (AS) | 2 |
| pEPG614 | ACC Syn cDNA (S) | 1 |
| pEPG612 | ACC Oxi cDNA (AS) + ACC Syn Geno (AS) | 50 |

Broccoli plants are also being produced with the use of pEPG610 and pEPG612. These are listed below.

| pEPG Plasmid | Genes | Line No. | Status |
|---|---|---|---|
| 610 | ACC Syn Geno (AS) | 290–101 | potted |
| 610 | ACC Syn Geno (AS) | 290–83 | potted |
| 610 | ACC Syn Geno (AS) | 290–6 | shoot |
| 610 | ACC Syn Geno (AS) | 336–66 | shoot |

What we claim is:

1. An isolated and purified DNA molecule encoding *Brassica olearacea* ACC synthase, wherein said DNA molecule comprises a nucleotide sequence selected from the group consisting of SEQ ID NO: 1 and SEQ ID NO:7.

2. A chimeric plant transformation cassette comprising the DNA molecule of claim 1, a promoter functional in plant cells, and a polyadenylation signal, wherein said promoter is operably linked to said DNA molecule, and said DNA molecule is operably linked to said polyadenylation signal.

3. The chimeric plant transformation cassette of claim 2 wherein said promoter is the CaMV 35S promoter.

4. The chimeric plant transformation cassette of claim 2 wherein said polyadenylation signal is the polyadenylation signal of the CaMV 35S gene.

5. The chimeric plant transformation cassette of claim 2 wherein the DNA molecule is in the antisense orientation.

6. A bacterial cell transformed with a vector comprising the chimeric plant transformation cassette of claim 2.

7. The bacterial cell of claim 6 wherein said bacterial cell is selected from the group consisting of an *Agrobacterium tumefaciens* cell and an *Agrobacterium rhizogenes* cell.

8. A transformed plant cell comprising the chimeric plant transformation cassette of claim 2.

9. The transformed plant cell of claim 8 wherein the promoter is the CaMV 35S promoter and the polyadenylation signal is the polyadenylation signal of the CaMV 35S gene.

10. A transgenic Brassica plant transformed with the chimeric plant transformation vector of claim 2.

11. The transgenic plant of claim 10 which is of the species *Brassica oleracea*.

12. A transformed plant seed comprising the chimeric plant transformation cassette of claim 2.

13. The transformed plant seed of claim 12 wherein the promoter is the CaMV 35S promoter and the polyadenylation signal is that of the CaMV 35S gene.

* * * * *

UNITED STATES PATENT AND TRADEMARK OFFICE
CERTIFICATE OF CORRECTION

PATENT NO. : 5,998,702
DATED : December 7, 1999
INVENTOR(S) : Boeshore et al.

It is certified that error appears in the above-identified patent and that said Letters Patent is hereby corrected as shown below:

Column 1,
Before "Field of the Invention," insert -- This application is a continuation-in-part of U.S. Serial No. 08/366,992 filed on December 30, 1994, now abandoned --.

Signed and Sealed this

Thirtieth Day of October, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1384 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 2..39

(ix) FEATURE:
      (A) NAME/KEY: CDS
      (B) LOCATION: 135..433

(ix) FEATURE:
      (A) NAME/KEY: CDS
      (B) LOCATION: 595..1383

(xi) SEQUENCE DESCRIPTION: SEQ ID NO:1:

C CAT GGG ATC AGC CAA ATG GGT CTT GCA GAG AAT CAG GT TATTATATTA   49

```
    His Gly Ile Ser Gln Met Gly Leu Ala Glu Asn Gln
      1               5                  10

TATACTTTTA TCAACCTTTC TTTCAAAAAA GTTAATTACA TATCGGATAT GTATTAATCG         109

TTTTTCTCTC GATCATTTTC TATAG GTC TCG TTC GAT CTT CTA GAA AGT TAC          161
                            Val Ser Phe Asp Leu Leu Glu Ser Tyr
                             1                   5

TTA GAG AAG AAA AAT CCA GAA GTT TCC ATG TGG GGA TCA AAA GGA GCA          209
Leu Glu Lys Lys Asn Pro Glu Val Ser Met Trp Gly Ser Lys Gly Ala
 10              15                  20                  25

CCT GGG TTC AGA GAA AAC GCA CTG TTT CAA GAC TAC CAC GGT CTC AAA          257
Pro Gly Phe Arg Glu Asn Ala Leu Phe Gln Asp Tyr His Gly Leu Lys
                 30                  35                  40

TCT TTC AGA CAA GCT ATG GCT AGC TTC ATG CAA CAG ATT CGT GGA GGC          305
Ser Phe Arg Gln Ala Met Ala Ser Phe Met Gln Gln Ile Arg Gly Gly
             45                  50                  55

AAA GCT AGA TTC GAC CCT GAC CGT ATC GTC CTC ACT GCT GGA GCC ACA          353
Lys Ala Arg Phe Asp Pro Asp Arg Ile Val Leu Thr Ala Gly Ala Thr
         60                  65                  70

GCC GCT AAT GAA CTC TTA ACG TTC ATC CTC GCT GAT CCC AAC GAC GCT          401
Ala Ala Asn Glu Leu Leu Thr Phe Ile Leu Ala Asp Pro Asn Asp Ala
     75                  80                  85

CTT CTC GTC CCT ACG CCA TAT TAT CCA GGG TA CGTCACATTT TATATTATTT         453
Leu Leu Val Pro Thr Pro Tyr Tyr Pro Gly
 90                  95

AAATAAAGAA TAATTAGTCA CTCGTATAGA GATTTTCTAT AATATTCAAA AAATAGCTGC         513

AACTAACTGA CACAAACTTA AAATAAAATA TTATCTACTA TATCTTGTAT TTACCGGAAC         573

GTTTATTTAT TTGAATACAG A TTC GAT AGA GAT TTG AGA TGG AGA ACA GGA          624
                         Phe Asp Arg Asp Leu Arg Trp Arg Thr Gly
                          1                   5                  10

GTG AGA ATT GTA CCG ATT CAT TGC GAC AGC TCC AAC CAT TTT CAG ATA          672
Val Arg Ile Val Pro Ile His Cys Asp Ser Ser Asn His Phe Gln Ile
                 15                  20                  25

ACC CCA GAG GCG CTC GAG CAG GCT TAC CAA ACG GCT CGT GAC GCG AAC          720
Thr Pro Glu Ala Leu Glu Gln Ala Tyr Gln Thr Ala Arg Asp Ala Asn
             30                  35                  40

ATT AGA GTC CGA GGA GTG CTC ATA ACC AAC CCA TCG AAC CCA TTA GGC          768
Ile Arg Val Arg Gly Val Leu Ile Thr Asn Pro Ser Asn Pro Leu Gly
         45                  50                  55

GCA ACG GTC CAA AAG AAG GTT CTA GAA GAT CTA CTT GAC TTC TGT GTA          816
Ala Thr Val Gln Lys Lys Val Leu Glu Asp Leu Leu Asp Phe Cys Val
     60                  65                  70

CGC AAG AAC ATT CAC TTG GTC TCA GAC GAG ATC TAC TCC GGG TCG GTC          864
Arg Lys Asn Ile His Leu Val Ser Asp Glu Ile Tyr Ser Gly Ser Val
 75                  80                  85                  90

TTC CAC GCG TCA GAA TTC ACC AGC GTA GCC GAG ATC GTA GAG AAC ATC          912
Phe His Ala Ser Glu Phe Thr Ser Val Ala Glu Ile Val Glu Asn Ile
                 95                 100                 105

GAT GAC GTG TCA GTC AAG GAA CGT GTC CAC ATC GTT TAC AGC CTC TCC          960
Asp Asp Val Ser Val Lys Glu Arg Val His Ile Val Tyr Ser Leu Ser
             110                 115                 120

AAA GAT CTA GGT CTT CCC GGT TTT CGA GTT GGG ACC ATT TAC TCG TAC         1008
Lys Asp Leu Gly Leu Pro Gly Phe Arg Val Gly Thr Ile Tyr Ser Tyr
         125                 130                 135

AAC GAT AAT GTT GTG AGG ACA GCG AGA AGG ATG TCG AGT TTC ACG CTT         1056
Asn Asp Asn Val Val Arg Thr Ala Arg Arg Met Ser Ser Phe Thr Leu
     140                 145                 150

GTC TCG TCT CAG ACA CAA CAC ATG TTG GCT TCC ATG TTG TCG GAT GAA         1104
Val Ser Ser Gln Thr Gln His Met Leu Ala Ser Met Leu Ser Asp Glu
 155                 160                 165                 170
```

```
GAG TTT ACG GAG AAG TAC ATA AGG ATA AAC CGT GAA AGG CTT AGG AGA      1152
Glu Phe Thr Glu Lys Tyr Ile Arg Ile Asn Arg Glu Arg Leu Arg Arg
                175                 180                 185

CGG TAC GAG ACA ATT GTG GAA GGG CTT AAG AAG GCA GGG ATC GAG TGT      1200
Arg Tyr Glu Thr Ile Val Glu Gly Leu Lys Lys Ala Gly Ile Glu Cys
            190                 195                 200

TTG AAG GGT AAT GCA GGG TTG TTC TGT TGG ATG AAT TTG GGT TTC TTG      1248
Leu Lys Gly Asn Ala Gly Leu Phe Cys Trp Met Asn Leu Gly Phe Leu
            205                 210                 215

CTC GAC ACG AAA ACG AAA CAA GGC GAG CTC GAG CTT TGG GAT GTG ATC      1296
Leu Asp Thr Lys Thr Lys Gln Gly Glu Leu Glu Leu Trp Asp Val Ile
            220                 225                 230

TTG AAG GAA CTA AAG CTG AAT ATA TCT CCT GGA TCT TCG TGC CAT TGC      1344
Leu Lys Glu Leu Lys Leu Asn Ile Ser Pro Gly Ser Ser Cys His Cys
235                 240                 245                 250

TCG GAG TAT GGA TGG TTT AGG ATT TGC TTT GCC ACC ATG G                1384
Ser Glu Tyr Gly Trp Phe Arg Ile Cys Phe Ala Thr Met
                255                 260
```

(2) INFORMATION FOR SEQ ID NO:2:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:2:

```
His Gly Ile Ser Gln Met Gly Leu Ala Glu Asn Gln
1               5                   10
```

(2) INFORMATION FOR SEQ ID NO:3:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO:3:

```
Val Ser Phe Asp Leu Leu Glu Ser Tyr Leu Glu Lys Lys Asn Pro Glu
1               5                   10                  15

Val Ser Met Trp Gly Ser Lys Gly Ala Pro Gly Phe Arg Glu Asn Ala
                20                  25                  30

Leu Phe Gln Asp Tyr His Gly Leu Lys Ser Phe Arg Gln Ala Met Ala
            35                  40                  45

Ser Phe Met Gln Gln Ile Arg Gly Gly Lys Ala Arg Phe Asp Pro Asp
        50                  55                  60

Arg Ile Val Leu Thr Ala Gly Ala Thr Ala Ala Asn Glu Leu Leu Thr
65                  70                  75                  80

Phe Ile Leu Ala Asp Pro Asn Asp Ala Leu Leu Val Pro Thr Pro Tyr
                85                  90                  95

Tyr Pro Gly
```

(2) INFORMATION FOR SEQ ID NO:4:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:4:

Phe Asp Arg Asp Leu Arg Trp Arg Thr Gly Val Arg Ile Val Pro Ile
1               5                   10                  15

His Cys Asp Ser Ser Asn His Phe Gln Ile Thr Pro Glu Ala Leu Glu
            20                  25                  30

Gln Ala Tyr Gln Thr Ala Arg Asp Ala Asn Ile Arg Val Arg Gly Val
        35                  40                  45

Leu Ile Thr Asn Pro Ser Asn Pro Leu Gly Ala Thr Val Gln Lys Lys
    50                  55                  60

Val Leu Glu Asp Leu Leu Asp Phe Cys Val Arg Lys Asn Ile His Leu
65              70                  75                  80

Val Ser Asp Glu Ile Tyr Ser Gly Ser Val Phe His Ala Ser Glu Phe
                85                  90                  95

Thr Ser Val Ala Glu Ile Val Glu Asn Ile Asp Asp Val Ser Val Lys
            100                 105                 110

Glu Arg Val His Ile Val Tyr Ser Leu Ser Lys Asp Leu Gly Leu Pro
        115                 120                 125

Gly Phe Arg Val Gly Thr Ile Tyr Ser Tyr Asn Asp Asn Val Val Arg
    130                 135                 140

Thr Ala Arg Arg Met Ser Ser Phe Thr Leu Val Ser Ser Gln Thr Gln
145                 150                 155                 160

His Met Leu Ala Ser Met Leu Ser Asp Glu Glu Phe Thr Glu Lys Tyr
                165                 170                 175

Ile Arg Ile Asn Arg Glu Arg Leu Arg Arg Arg Tyr Glu Thr Ile Val
            180                 185                 190

Glu Gly Leu Lys Lys Ala Gly Ile Glu Cys Leu Lys Gly Asn Ala Gly
        195                 200                 205

Leu Phe Cys Trp Met Asn Leu Gly Phe Leu Leu Asp Thr Lys Thr Lys
    210                 215                 220

Gln Gly Glu Leu Glu Leu Trp Asp Val Ile Leu Lys Glu Leu Lys Leu
225                 230                 235                 240

Asn Ile Ser Pro Gly Ser Ser Cys His Cys Ser Glu Tyr Gly Trp Phe
                245                 250                 255

Arg Ile Cys Phe Ala Thr Met
            260

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCATGGGATC ATCCAAATGG GTCTTGCAGA G                                31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCTACCAAAT CCTAAACGAA ACGGTGGTAC C          31

(2) INFORMATION FOR SEQ ID NO:7:

(i) SEQUENCE CHARACTERISTICS:
      (A) LENGTH: 994 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 3..975

(xi) SEQUENCE DESCRIPTION: SEQ ID NO:7:

```
CC ATG GGG GGA TCA AAA GGA GCA CCT GGG TTC AGA GAA AAC GCA CTG        47
   Met Gly Gly Ser Lys Gly Ala Pro Gly Phe Arg Glu Asn Ala Leu
   1               5                  10                  15

TTT CAA GAC TAC CAC GGT CTC AAA TCT TTC AGA CAA GCT ATG GCT AGC       95
Phe Gln Asp Tyr His Gly Leu Lys Ser Phe Arg Gln Ala Met Ala Ser
                20                  25                  30

TTC ATG CAA CAG ATT CGT GGA GGC AAA GCT AGA TTC GAC CCT GAC CGT      143
Phe Met Gln Gln Ile Arg Gly Gly Lys Ala Arg Phe Asp Pro Asp Arg
            35                  40                  45

ATC GTC CTC ACT GCT GGA GCC ACA GCC GCT AAT GAA CTC TTA ACG TTC      191
Ile Val Leu Thr Ala Gly Ala Thr Ala Ala Asn Glu Leu Leu Thr Phe
        50                  55                  60

ATC CTC GCT GAT CCC AAC GAC GCT CTT CTC GTC CCT ACG CCA TAT TAT      239
Ile Leu Ala Asp Pro Asn Asp Ala Leu Leu Val Pro Thr Pro Tyr Tyr
    65                  70                  75

CCA GGA TTC GAT AGA GAT TTG AGA TGG AGA ACC GGA GTG AGA ATT GTA      287
Pro Gly Phe Asp Arg Asp Leu Arg Trp Arg Thr Gly Val Arg Ile Val
80                  85                  90                  95

CCG ATT CAT TGC GAC AGC TCC AAC CAT TTT CAG ATA ACC CCA GAG GCG      335
Pro Ile His Cys Asp Ser Ser Asn His Phe Gln Ile Thr Pro Glu Ala
                100                 105                 110

CTC GAG CAG GCT TAC CAA ACG GCT CGT GAC GCG AAC ATT AGA GTC CGA      383
Leu Glu Gln Ala Tyr Gln Thr Ala Arg Asp Ala Asn Ile Arg Val Arg
            115                 120                 125

GGA GTG CTC ATA ACC AAC CCA TCG AAC CCA TTA GGC GCA ACG TCC AA       431
Gly Val Leu Ile Thr Asn Pro Ser Asn Pro Leu Gly Ala Thr Val Gln
        130                 135                 140

AAG AAG GTT CTA GAA GAT CTA CTT GAC TTC TGT GTA CGC AAG AAC ATC      479
Lys Lys Val Leu Glu Asp Leu Leu Asp Phe Cys Val Arg Lys Asn Ile
    145                 150                 155

CAC TTG GTC TCA GAC GAG ATC TAC TCC GGG TCG GTC TTC CAC GCG TCA      527
His Leu Val Ser Asp Glu Ile Tyr Ser Gly Ser Val Phe His Ala Ser
160                 165                 170                 175

GAA TTC ACC AGC GTA GCC GAG ATC GTA GAG AAC ATC GAT GAC GTG TCA      575
Glu Phe Thr Ser Val Ala Glu Ile Val Glu Asn Ile Asp Asp Val Ser
                180                 185                 190

GTC AAG GAA CGT GTC CAC ATC GTT TAC AGC CTC TCC AAA GAT CTA GGT      623
Val Lys Glu Arg Val His Ile Val Tyr Ser Leu Ser Lys Asp Leu Gly
            195                 200                 205

CTT CCC GGT TTT CGA GTT GGG ACC ATT TAC TCG TAC AAC GAT AAT GTT      671
Leu Pro Gly Phe Arg Val Gly Thr Ile Tyr Ser Tyr Asn Asp Asn Val
        210                 215                 220

GTG AGG ACA GCG AGA AGG ATG TCG AGT TTC ACG CTT GTC TCG TCT CAG      719
Val Arg Thr Ala Arg Arg Met Ser Ser Phe Thr Leu Val Ser Ser Gln
```

```
                    225                 230                 235
ACA CAA CAC ATG TTG GCT TCC ATG TTG TCG GAT GAA GAG TTT ACG GAG      767
Thr Gln His Met Leu Ala Ser Met Leu Ser Asp Glu Glu Phe Thr Glu
240                     245                 250                 255

AAG TAC ATA AGG ATA AAC CGT GAA AGG CTT AGG AGA CGG TAC GAG ACA      815
Lys Tyr Ile Arg Ile Asn Arg Glu Arg Leu Arg Arg Arg Tyr Glu Thr
                        260                 265                 270

ATT GTG GAA GGG CTT AAG AAG GCA GGG ATC GAG TGT TTG AAG GGT AAT      863
Ile Val Glu Gly Leu Lys Lys Ala Gly Ile Glu Cys Leu Lys Gly Asn
                275                 280                 285

GCA GGT TTG TTC TGT TGG ATG AAT TTG GGT TTC TTG CTC GAC ACG AAA      911
Ala Gly Leu Phe Cys Trp Met Asn Leu Gly Phe Leu Leu Asp Thr Lys
            290                 295                 300

ACG AAA CAA GGC GAG CTC GAG CTT TGG GAT GTG ATC TTG GAG GAA CTA      959
Thr Lys Gln Gly Glu Leu Glu Leu Trp Asp Val Ile Leu Glu Glu Leu
        305                 310                 315

AAG CTG AAT ATA TCT  C CTGATCTTCG TGCCATGGC                          994
Lys Leu Asn Ile Ser
320
```

(2) INFORMATION FOR SEQ ID NO:8:

(i) SEQUENCE CHARACTERISTICS:
        (A) LENGTH: 324 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Gly Ser Lys Gly Ala Pro Gly Phe Arg Glu Asn Ala Leu Phe
1               5                   10                  15

Gln Asp Tyr His Gly Leu Lys Ser Phe Arg Gln Ala Met Ala Ser Phe
                20                  25                  30

Met Gln Gln Ile Arg Gly Gly Lys Ala Arg Phe Asp Pro Asp Arg Ile
            35                  40                  45

Val Leu Thr Ala Gly Ala Thr Ala Ala Asn Glu Leu Leu Thr Phe Ile
        50                  55                  60

Leu Ala Asp Pro Asn Asp Ala Leu Leu Val Pro Thr Pro Tyr Tyr Pro
65                  70                  75                  80

Gly Phe Asp Arg Asp Leu Arg Trp Arg Thr Gly Val Arg Ile Val Pro
                85                  90                  95

Ile His Cys Asp Ser Ser Asn His Phe Gln Ile Thr Pro Glu Ala Leu
            100                 105                 110

Glu Gln Ala Tyr Gln Thr Ala Arg Asp Ala Asn Ile Arg Val Arg Gly
        115                 120                 125

Val Leu Ile Thr Asn Pro Ser Asn Pro Leu Gly Ala Thr Val Gln Lys
    130                 135                 140

Lys Val Leu Glu Asp Leu Leu Asp Phe Cys Val Arg Lys Asn Ile His
145                 150                 155                 160

Leu Val Ser Asp Glu Ile Tyr Ser Gly Ser Val Phe His Ala Ser Glu
                165                 170                 175

Phe Thr Ser Val Ala Glu Ile Val Glu Asn Ile Asp Asp Val Ser Val
            180                 185                 190

Lys Glu Arg Val His Ile Val Tyr Ser Leu Ser Lys Asp Leu Gly Leu
        195                 200                 205

Pro Gly Phe Arg Val Gly Thr Ile Tyr Ser Tyr Asn Asp Asn Val Val
    210                 215                 220
```

```
Arg Thr Ala Arg Arg Met Ser Ser Phe Thr Leu Val Ser Ser Gln Thr
225                 230                 235                 240

Gln His Met Leu Ala Ser Met Leu Ser Asp Glu Glu Phe Thr Glu Lys
                245                 250                 255

Tyr Ile Arg Ile Asn Arg Glu Arg Leu Arg Arg Arg Tyr Glu Thr Ile
                260                 265                 270

Val Glu Gly Leu Lys Lys Ala Gly Ile Glu Cys Leu Lys Gly Asn Ala
            275                 280                 285

Gly Leu Phe Cys Trp Met Asn Leu Gly Phe Leu Leu Asp Thr Lys Thr
290                 295                 300

Lys Gln Gly Glu Leu Glu Leu Trp Asp Val Ile Leu Glu Glu Leu Lys
305                 310                 315                 320

Leu Asn Ile Ser
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GTTTCCATGG GGGGATCAAA AGGAGC                                    26
```

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GGACTAGAAG CACGGTACCG AGCC                                      24
```

(2) INFORMATION FOR SEQ ID NO:11:

(i) SEQUENCE CHARACTERISTICS:
        (A) LENGTH: 1497 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CGGGCAACAG AACAACAAAA AAACACAGCT TATTAAAACC CCTTTGAGGA AACAAGAGAA    60

ACAAAAATGG TAGCTTTGAC TGCAGAGAAG CAAGATCAGA ACCTACTGTC AAGAATGGCC   120

GCCGGTGACG GTCACGGCGA GAATTCAGCT TATTTCGACG GCTGGAAAGC TTATGAAGAA   180

AACCCATTTC ACCCAATTAA CAGACCCGAT GGAGTTATTC AGATGGGTCT CGCTGAAAAT   240

CAGCTTTGTG GAGATTTGAT GCGTAAATGG GTTTTAGAAC ATCCAGAAGC TTCGATTTGC   300

ACAGCAGAAG GTGTGAATCA GTTCAGCGAC ATTGCAATTT TCCAGGACTA CCATGGCTTG   360

CCCGAGTTCA GACAAGCTGT AGCGAAGTTT ATGGAGAAGA CAAGAAACAA CAAAGTGAGG   420

TTTGATCCTG ATCGGATTGT CATGAGCGGC GGTGCAACCG GAGCACACGA GACGGTTGCT   480

TTCTGTTTAG CCAATACCGG CGAAGGTTTC TTGGTTCCGA CTCCTTATTA TCCAGGGTTT   540
```

-continued

```
GATAGAGATT TGAGATGGAG AACCGGAGTG AATCTTGTAC CGGTTACTTG TCATAGCTCT      600

AACGGGTTTA AGATCACGGT GGAAGCCTTG GAAGCTGCGT ACGAAAACGC GCGTGTATCC      660

AACATTCCCG TTAAGGGTTT ACTCATAACC AATCCTTCGA ACCCGCTTGG TACGACGTTA      720

GACCGGGATT GCTTGAAATC TTTGGTTAAC TTCACCAATA ACAAGGGGAT CCACCTCATT      780

GCTGATGAGA TCTATGCAGC CACTACTTTT GGTCAATCCG AGTTCATAAG TGTTGCAGAA      840

GTCATCGAGG AGGTCCCACA TTCGAACCGC GATTTGATCC ATATTGTGTA TAGCCTATCA      900

AAAGATATGG GTTTGCCCGG TTTAAGAGTC GGTATAGTAT ACTCTTACAA TGACCGGGTG      960

GTTCAAATTG CTAGGAAAAT GTCGAGTTTC GGTTTGGTCT CGTCTCAAAC GCAGCATCTG     1020

ATCGCCAAAA TGTTATCCGA CGAAGACTTT GTAGACGAAT TCATCCGCAA GAGCAAACTA     1080

CGGTTAGCTG CAAGACACGC AGAGTTAACA ACCGGTTTAG ACGGTTTAGG CATTGGTTGG     1140

TTAAAGGCCG GAGCCGGTTT GTTCATCTGG ATGGATTTAA GAAACCTTTT GAAGACAGCT     1200

ACATTCGACT CAGAGATGGA GCTGTGGCGT GTGATCGCTA CCAACAAGGT GAAGCTTAAC     1260

GTTTCTCCAG GCGGTTCGTG CCATTGCAAC GAACCGGGAT GGTTTAGTAT GTTTGCGAAC     1320

ATGGACCACA AGACCATGGA GACAGCTCTA GAGAGGATCA GAGTGTTCAC TAGTCAACTT     1380

GAGGAGGAGA GTCTGAAACA GACTAAACCA ATGGCTGCAC CAACTGTGAT GGCTAAGAAG     1440

AAGATGTGTT GGCAGAGTAG CCTCCGGTTA AGCTTTAAGG ACACGAGACG TTTCGAG        1497
```